United States Patent
Ojima et al.

(10) Patent No.: US 10,029,014 B2
(45) Date of Patent: Jul. 24, 2018

(54) SYNTHESIS OF NOVEL ASYMMETRIC BOW-TIE PAMAM DENDRIMER-BASED CONJUGATES FOR TUMOR-TARGETING DRUG DELIVERY

(71) Applicant: THE RESEARCH FOUNDATION FOR THE STATE UNIVERSITY OF NEW YORK, Albany, NY (US)

(72) Inventors: Iwao Ojima, Port Jefferson, NY (US); Tao Wang, Tianjin (CN); Yu-Han Teng, Hualien County (TW)

(73) Assignee: THE RESEARCH FOUNDATION FOR THE STATE UNIVERSITY OF NEW YORK, Albany, NY (US)

(*) Notice: Subject to any disclaimer, the term of this patent is extended or adjusted under 35 U.S.C. 154(b) by 0 days.

(21) Appl. No.: 14/917,344

(22) PCT Filed: Sep. 9, 2014

(86) PCT No.: PCT/US2014/054655
§ 371 (c)(1),
(2) Date: Mar. 8, 2016

(87) PCT Pub. No.: WO2015/038493
PCT Pub. Date: Mar. 19, 2015

(65) Prior Publication Data
US 2016/0220688 A1     Aug. 4, 2016

Related U.S. Application Data

(60) Provisional application No. 61/875,943, filed on Sep. 10, 2013, provisional application No. 62/035,794, filed on Aug. 11, 2014.

(51) Int. Cl.
| | | |
|---|---|---|
| *A61K 31/415* | (2006.01) |
| *A61K 47/48* | (2006.01) |
| *C07D 305/14* | (2006.01) |
| *C07D 407/12* | (2006.01) |
| *C07D 495/04* | (2006.01) |
| *C07D 207/452* | (2006.01) |
| *A61K 31/337* | (2006.01) |
| *A61K 47/60* | (2017.01) |
| *A61K 47/54* | (2017.01) |
| *A61K 47/59* | (2017.01) |

(52) U.S. Cl.
CPC ...... *A61K 47/48207* (2013.01); *A61K 31/337* (2013.01); *A61K 47/545* (2017.08); *A61K 47/595* (2017.08); *A61K 47/60* (2017.08); *C07D 207/452* (2013.01); *C07D 305/14* (2013.01); *C07D 407/12* (2013.01); *C07D 495/04* (2013.01)

(58) Field of Classification Search
CPC .......... A61K 31/337; A61K 47/48061; A61K 47/48207; A61K 47/48215; A61K 47/545; A61K 47/595; A61K 47/60; C07D 207/452; C07D 305/14; C07D 407/12; C07D 495/04
USPC ........................................ 514/387
See application file for complete search history.

(56) References Cited

U.S. PATENT DOCUMENTS

| | | | |
|---|---|---|---|
| 2007/0041934 A1 | 2/2007 | William et al. | |
| 2009/0208580 A1 | 8/2009 | Shi et al. | |
| 2011/0076233 A1* | 3/2011 | McBride ............ | A61K 31/4745 424/1.57 |

FOREIGN PATENT DOCUMENTS

| | | |
|---|---|---|
| WO | WO 2010/147831 A1 | 12/2010 |
| WO | WO 2011/008992 A2 | 1/2011 |
| WO | WO 2011/059609 A2 | 5/2011 |

OTHER PUBLICATIONS

Wang et al., "Synthesis of a Novel Asymmetrical Bow-tie PAMAM Dendrimer-based Drug Conjugate Bearing Biotin and a Second-generation Taxoid", Jul. 6, 2012, 244th National ACS meeting abstracts (Aug. 19-23, 2012), pp. MEDI 69.*

(Continued)

*Primary Examiner* — My-Chau T. Tran
(74) *Attorney, Agent, or Firm* — Scully Scott Murphy and Presser

(57) ABSTRACT

The present disclosure relates to a dendrimer-based conjugate of the formula $V_m$-D-C-D'-$(T-F)_n$, which is useful for tumor targeting drug delivery. The use of asymmetric dendrimers allow for specific targeting as well as synthetic reproducibility.

21 Claims, 6 Drawing Sheets

(56) References Cited

OTHER PUBLICATIONS

Trembleau et al., "Development of 18F-fluorinatable dendrons and their application to cancer cell targeting", 2011, New Journal of Chemistry, 35(11), pp. 2496-2502.*

Qiao et al., "Synthesis and characterization of multi-functional linear-dendritic block copolymer for intracellular delivery of antitumor drugs", International Journal of Pharmaceutics, Aug. 16, 2013, 452(1-2), pp. 363-373.*

Wang et al., "Synthesis and biological evaluation of novel asymmetric bow-tie PAMAM dendrimer-based tumor-targeting drug conjugates", Sep. 8, 2013, 246th National ACS meeting abstracts (Sep. 8-12, 2013), pp. MEDI 231. (Year: 2013).*

Wang et al., "Design, synthesis, and development of a novel PAMAM-based bow-tie dendrimer platform for tumor-targeting drug delivery", Aug. 10, 2014, 248th National ACS meeting abstracts (Aug. 10-14, 2014), pp. MEDI 456. (Year: 2014).*

Wang et al., "Design and synthesis of a novel tri-branched asymmetric bowtie PAMAM dendrimer-based drug conjugate as a cancer theranostic agent", Mar. 22, 2015, 249th National ACS meeting abstracts (Mar. 22-26, 2015), pp. MEDI 121. (Year: 2015).*

Gingras M. et al., "Cleavable Dendrimers", Angew. Chem. Int. Ed. 46:1010-1017 (2007).

International Search Report dated Dec. 4, 2014 issue in PCT/US2014/054655.

* cited by examiner

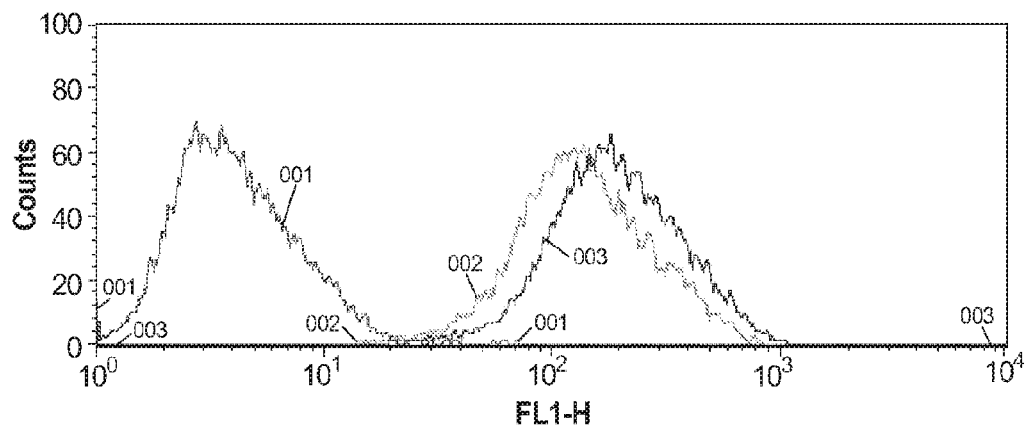
*Fig. 5A*
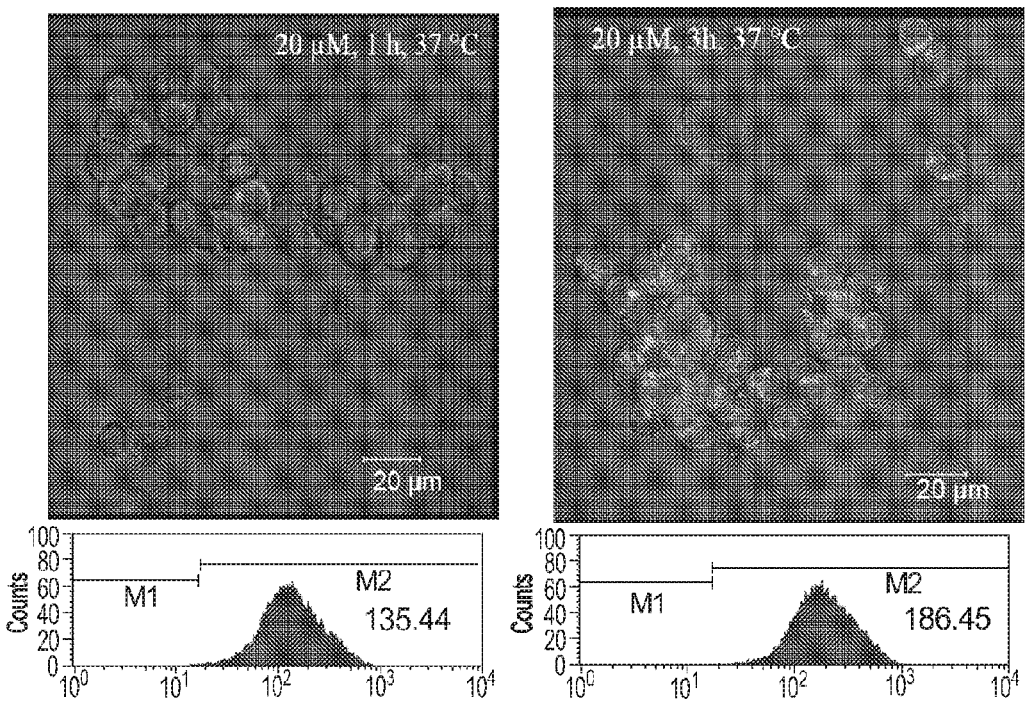
*Fig. 5B*  *Fig. 5C*

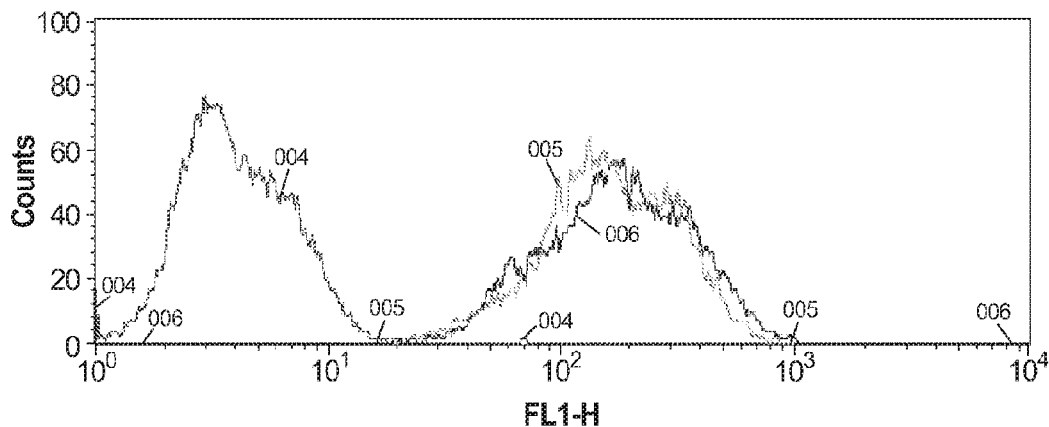
*Fig. 5D*
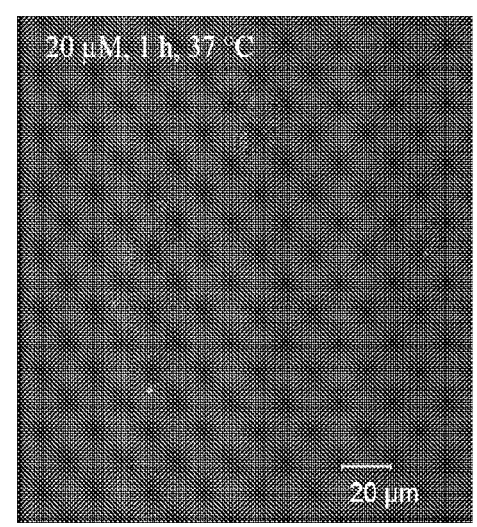
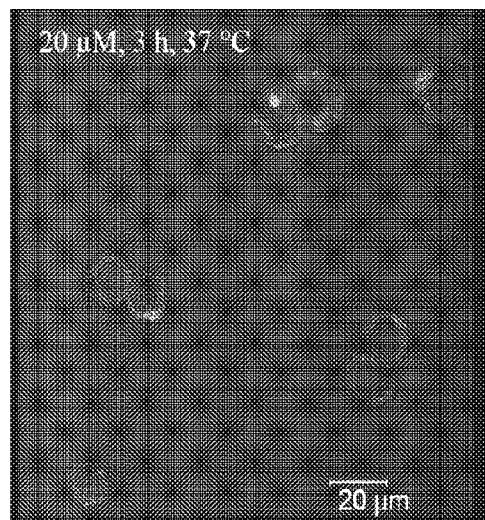
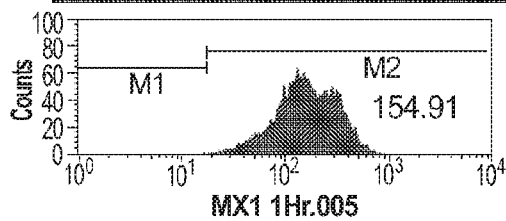
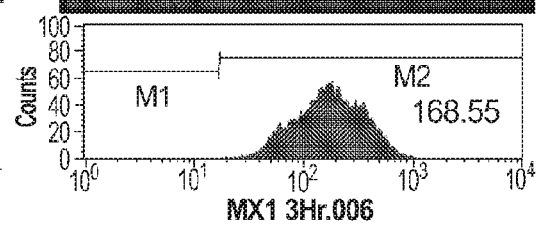
*Fig. 5E*        *Fig. 5F*

SYNTHESIS OF NOVEL ASYMMETRIC BOW-TIE PAMAM DENDRIMER-BASED CONJUGATES FOR TUMOR-TARGETING DRUG DELIVERY

This application claims benefit of U.S. Provisional Application No. 61/875,943, filed Sep. 10, 2013, and U.S. Provisional Application No. 62/035,794, filed Aug. 11, 2014, the entire contents of which are incorporated herein by reference.

STATEMENT REGARDING FEDERALLY SPONSORED RESEARCH

The present invention was made with government support under grant number CA103314 awarded by the National Institute of Health (NIH). The government has certain rights in the invention.

BACKGROUND OF THE DISCLOSURE

Cancer is a leading cause of death in the United States. Despite the significant progress in the development of cancer detection, prevention, surgery, chemotherapy and radiation therapy, no common cure has been fully established for patients with these malignant diseases. Traditional chemotherapy relies on the premise that rapidly proliferating tumor cells are more likely to be killed by cytotoxic agents than normal cells. However, due to the little or no specificity of these cytotoxic agents, severe systemic toxicity and dose-limiting side effects may occur.

Tumor-targeting drug conjugates are designed with a tumor recognition moiety attached directly, or through a linker, to a cytotoxic agent. Synthesizing a tumor-targeting drug conjugate that is stable during blood circulation but readily cleaved to release the cytotoxic agent efficiently upon internalization into the tumor cells is, however, not always feasible. In addition, binding a cytotoxic agent to a recognition moiety can have the effect of dramatically reducing the efficacy of the cytotoxic agent, or disabling the action of the cytoxic agent completely.

Tumor-targeting prodrug delivery strategies are based on active or passive targeting. Active targeting relies on the difference between tumor-associated cell surface biomarker expression, such as antigen or receptor, and cell surface biomarker expression in normal tissue. In the past, numerous research efforts have focused on conjugating anticancer drugs with antibodies through a linker to construct a tumor-targeting drug conjugate for drug delivery. For example, monoclonal antibodies were intensively investigated in active targeting approaches because of their high binding affinity for the responding antigens.

Another more challenging strategy, classified as passive targeting, employs macromolecules, including polymers or nanoparticles, as inactive carriers or vehicles. These macromolecules are not directly interacting with tumor cells, but strongly influence the accumulation, transportation and biodistribution of their drug conjugates in tumor tissue due to the enhanced permeability and retention effect.

Dendrimer chemistry was first discovered in the 1970's. In the 1980's, the first family of dendrimers with controlled molecular weight building, controlled branching and versatility in design and modification of the reactive terminal end groups was realized.

Compared with the small molecular drug conjugates which only have a limited number of targeting moieties in each conjugate, a dendrimer employed as a macromolecular carrier can largely increase the loading capacity of the targeting moiety to achieve a high targeting concentration and efficiency at tumor sites.

It is a common issue in the polymeric medicinal chemistry field that the polymer-derived macromolecules are not a single component. Due to the steric hindrance effect of dendrimers and limitations in the purification thereof, functionalization of the surface of dendrimers usually generates multi-component derivatives which only have slight chemical differences, which result in separation difficulties. In addition, the quality of each batch depends on many factors including reaction time, temperature and reaction solvents. It is thus no guarantee that a multi-functionalized dendrimer can exhibit the same functionalities consistently. This leads to practically irreproducible results from batch to batch.

Thus, there is a need for improving, inter alia, the specificity of cytotoxic agent delivery and of tumor recognition. To achieve the above, there is a need for an improved tumor recognition moiety as well as an appropriate cleavable linker that binds the tumor recognition moiety to the cytotoxic agent.

SUMMARY OF THE DISCLOSURE

The disclosure relates to an improved dendrimer-based conjugate which has the ability to selectively deliver a targeted dose of one or more cytotoxic agents within a subject to a specific area, such as a cancer cell.

These, and other objectives as will be apparent to those of ordinary skill in the art, have been achieved by providing a dendrimer-based conjugate having the formula $V_m$-D-C-D'-$(T-F)_n$, wherein:

V is a tumor-targeting molecule that may be optionally contain a moiety inserted between V and D. The tumor targeting molecule can be any molecule capable recognizing or binding to a specific area of the body. Non-limiting examples of tumor-targeting molecules include biotin, antibodies, fragments of antibodies, fragments of antibodies, monoclonal antibodies, a protein, a peptide, oligopeptides, aptamers, hyaluronic acid, lectin, a saccharide, a hormone, polyunsaturated fatty acids, folic acid, transferrin or a neurotransmitter. Non-limiting examples of moieties that may be inserted between V and D include polyamino acid, such as polyglycine, polylysine, polytyrosine and polyphenylalanine, dextran, polysaccharides, polypropylene oxide (PPO), poly D-amino acids, a copolymer of polyethylene glycol (PEG) with PPO, PEG, polyglycolic acid, polyvinyl pyrolidone, polylactic acid and polyvinylalcohol or a mixture thereof. m and n are the same or different and can be 1 to 64.

D is a dendrimer. Non-limiting examples of dendrimers include PAMAM (poly(amidoamine)), PAMAMOS (poly(amidoamine-organosilicon)dendrimers), PPI (poly(propylene imine)), amphiphilic dendrimer, chiral dendrimer, multilingual dendrimer, micellar dendrimer, Tecto dendrimer and Frechet type dendrimer.

C is any cleavable functionality that may optionally contain a spacer moiety. Non-limiting examples of cleavable functionalities include cystamine, and those described in Angew. Chem. Int. Ed., 2007, 46, 1010-1017 (incorporated herein by reference). Non-limiting examples of optional spacer moieties include PEGylated bis-maleimido, carbamates, thiocarbamates, carbonate groups, thiocarbonate groups, ureas, thioureashydrazones, cis-aconityls, bifunctional peptides and bis-bromo compounds.

D' is a dendrimer. Preferably D' is a dendrimer that differs from dendrimer D, in either differing generations and/or differing structure.

T is a cytotoxic agent. Non-limiting examples of cytotoxic agents include paclitaxel, taxoids such as docetaxel, cabazitaxel and SB-T-1214, vinca alkaloids such as vinblastine and vincristine, desacetyl vinblastine and desacetyl vinblastine hydrazine, anthracyclines such as doxorubicin, daunorubicin, morpholino-doxorubicin and cyanomorpholino-doxorubicin, geldanamycin, ricin, abrin, diphtheria toxin, modecin, tetanus toxin, mycotoxins, mellitin, α-amanitin, pokeweed antiviral protein, ribosome inhibiting proteins, auristatin E, auristatin EB (AEB), auristatin EFP (AEFP), monomethyl auristatin E (MMAE), 5-benzoylvaleric acid-AE ester (AEVB), tubulysins, disorazole, epothilones, SN-38, topotecan, rhizoxin, duocarmycin, actinomycin, ansamitocin-P3, duocarmycin, duocarmycin B2, maytansine, maytensinoids (DM1, DM2, DM3, DM4), calicheamicin, echinomycin, colchicine, estramustine, cemadotin, eleutherobin, 1-hydroxyauramycin A, aclacinomycin, abafilomycin C1, dinaktin, dolastatin such as dolestatin-10, combretastatin, leptomycin B, pluramycins, staurosporine, nogalamycin, rhodomycins, mithramycin, rabelomycin, rapamycin, alnumycin, chartreusin, geliomycin, gilvocarcin, piericidin, chlorambucil, cyclophosphamide, melphalan, and antimetabolites such as methotrexate, dichlorormethatrexate, methopterin, cytosine arabinoside, leurosine, leurosideine, mitomycin C, mitomycin A, carminomycin, aminopterin, tallysomycin, podophyllotoxin, camptothecin.

F is optionally a fluorescent tagging molecule. Non-limiting examples of fluorescent tagging molecules include fluorescein and its derivatvies, rhodamine and its derivatives, coumarin and its derivatives, boron dipyrromethane (BODIPY) fluorophore derivatives, naphthalimide derivatives (Lucifer Yellow), maleimide and its derivatives, and/or radionuclides such as, but not limited to, radiohalides or a metal chelator carrying radionuclide.

BRIEF DESCRIPTION OF THE DRAWINGS

FIGS. 5A-F. CFM images and flow cytometry analysis of different types of cells with ABTD-3 at the final concentration of 20 μM at 37° C. for different periods: (A) flow cytometry analysis of ABTD-3 in ID-8 at 0 h, 1 h and 3 h; (B) CFM images and flow cytometry analysis in ID-8 at 1 h; (C) CFM images and flow cytometry analysis in ID-8 at 3 h; (D) flow cytometry analysis of ABTD-3 in MX-1 at 0 h, 1 h and 3 h; (E) CFM images and flow cytometry analysis in MX-1 at 1 h; (F) CFM images and flow cytometry analysis in MX-1 at 3 h.

DETAILED DESCRIPTION OF THE DISCLOSURE

Figure 1:
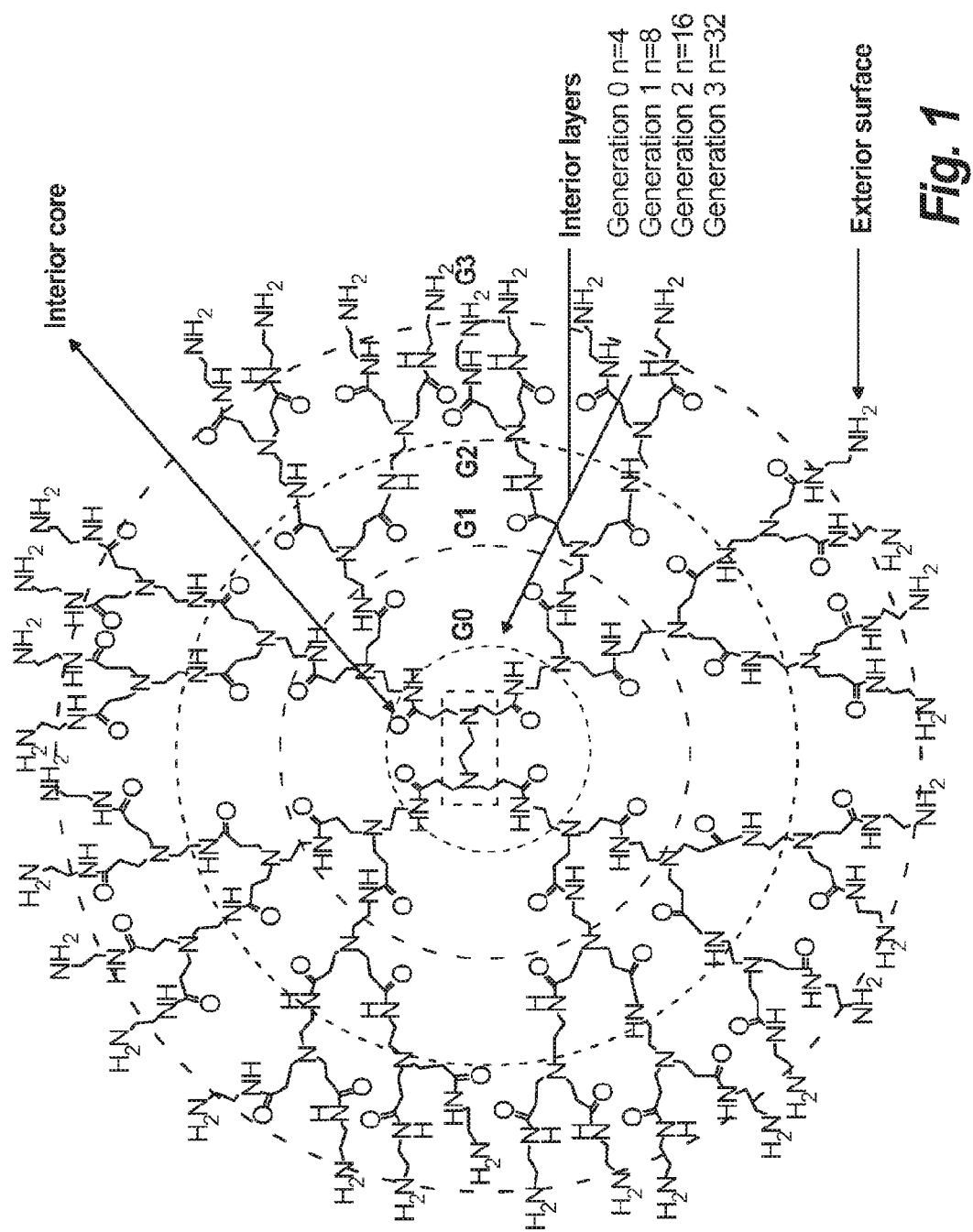
FIG. 1. Third generation PAMAM dendrimer showing the interior core and exterior surface of the dendrimer.
Figure 2:
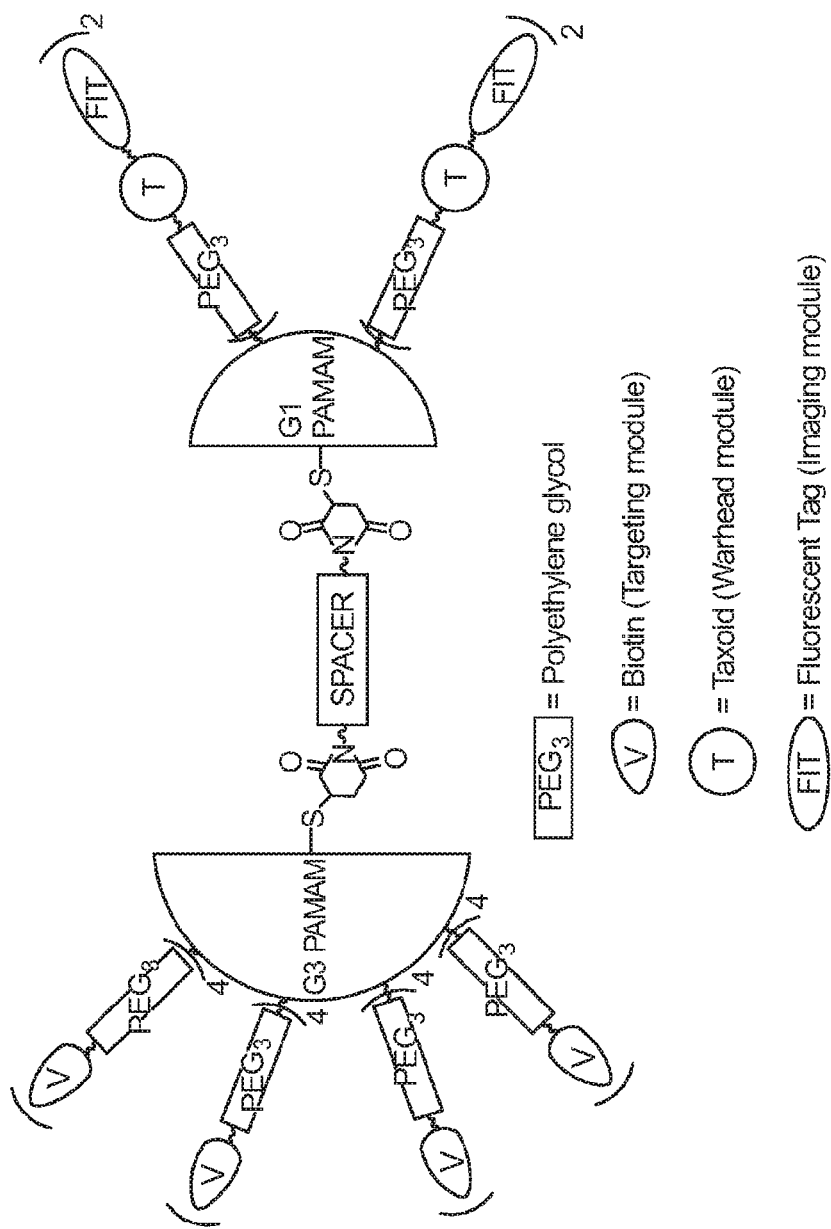
FIG. 2. An example of the PAMAM-based asymmetric bow-tie dendrimer (ABTD) platform.
Figure 3:
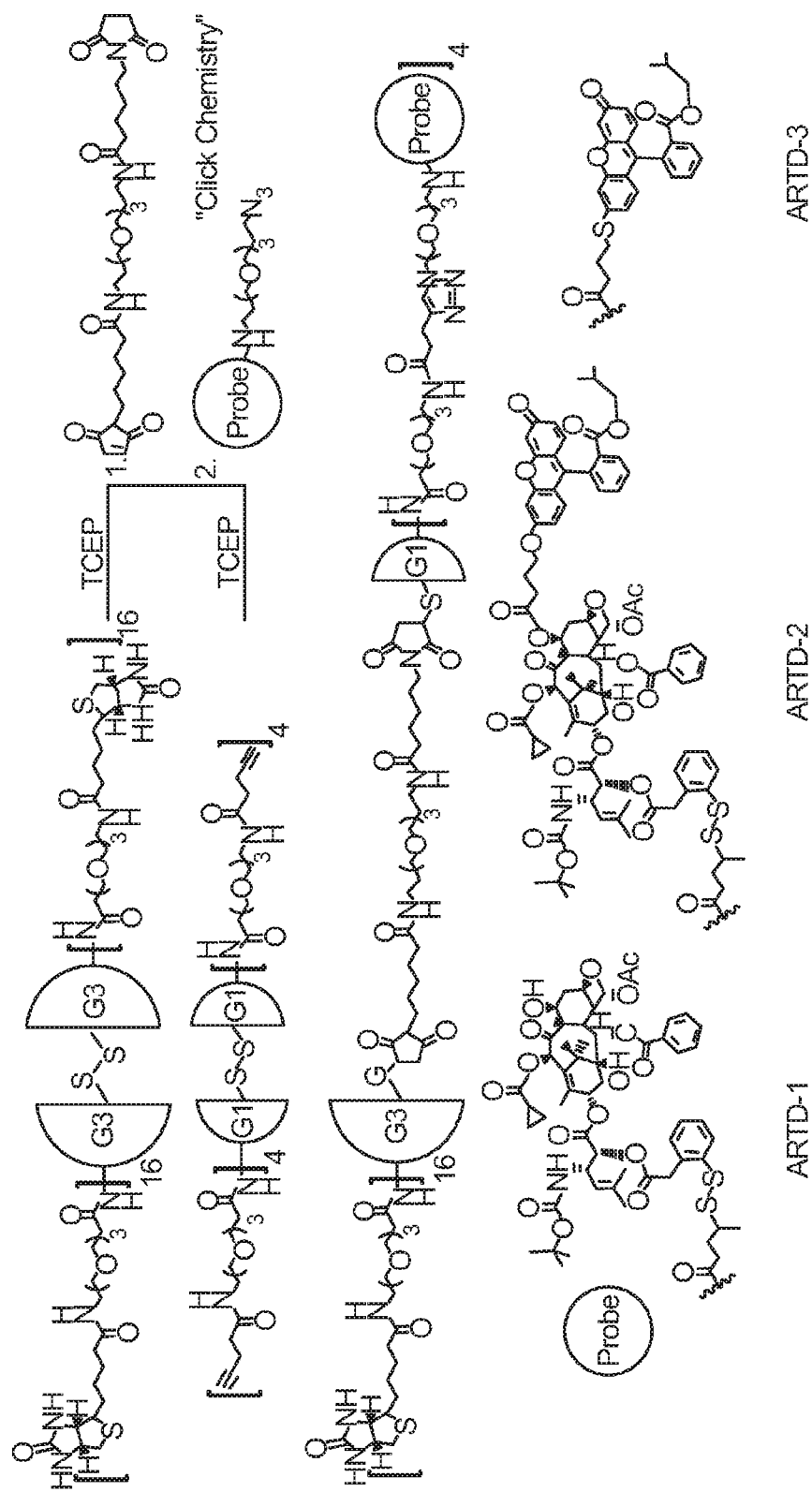
FIG. 3. Synthesis of PAMAM-based asymmetric bow-tie dendrimer (ABTD) conjugates.

In the context of the present disclosure, the following definitions apply:

The term "dendrimer" is intended to mean a class of polymers which are also known as starburst polymers because of their shapes (see FIG. 1). In general, a dendrimer exhibits a tree-like molecular architecture with an interior core, interior layers (also called "generations") which consist of repeating units regularly attached to the core, and an exterior surface of functional terminal groups attached to the outermost generation. Generation Number (usually abbreviated to G#) is determined by the number of focal points going from the core towards the surface. The molecular weight of the dendrimer itself and the number of terminal functional groups can easily be determined by the generation.

The term "cytotoxic agent" is intended to mean an agent, which is capable of reducing the number of cells and/or eliminating the cells that the targeting molecule is directed against. Said cytotoxic agent may be any kind of compound as long as the compound reduces the number of target cells and/or eliminates the targeted cells. The cytotoxic agent may assert its effect(s) by acting on the vital cell function or through irradiation. Examples of cytotoxic agents can be found in the following disclosure.

The terms "targeting molecule" and "tumor-targeting molecule" are intended to mean any agent that is capable of specifically targeting or interacting with specific cells within a subject, such as a human. Examples of tumor-targeting molecules can be found in the following disclosure.

The term "target" is intended to mean any structural element that the targeting molecule is directed against and to which the targeting molecule specifically interacts and thereby provides selectivity or preference towards the target. Non-limiting examples are molecules, which are produced in high amounts, such as cell surface structures overexpressed on different cancer cells and neovascular structural elements regulating angiogeneses. Preference is given to targets where the dendrimer linked to the targeting agent can be internalized and thereby release the cytotoxic agents inside the target cell. However, reduction of the undesirable target may also be achieved through extracellular release of the cytotoxic agents in the vicinity of the target or by intracellularly released cytotoxic agents leaking out from the target cells, so called by-standard effect.

The term "cancer" is intended to mean a neoplastic disease regardless of its histological origin. Non-limiting examples of cancer include haematological cancer, such as, but not limited to various types of leukemia, lymphoma and multiple myeloma as well as solid tumors, such as, but not limited to, breast cancer, ovarian cancer, lung cancer, colon cancer, head cancer, neck cancer, CNS tumor, prostate cancer, bone cancer and liver cancer.

The term "fluorescent tagging molecule" is intended to mean a compound that has a structural element that absorbs or emits UV and/or visible light or emits radiation, such as, but not limited to gamma-radiation. These structural elements may be, for example, fluorescent, chemiluminescent, or radioactive. Non-limiting examples include chromophores, bioluminescent compounds or diagnostic detector molecules, such as fluorescein and its derivatvies, rhodamine and its derivatives, coumarin and its derivatives, boron dipyrromethane (BODIPY) fluorophore derivatives, naphthalimide derivatives (Lucifer Yellow), maleimide and its derivatives, and/or radionuclides such as, but not limited to, radiohalides or a metal chelator carrying radionuclide.

The disclosure provides a dendrimer-based conjugate having the formula $V_m$-D-C-D'-(T-F)$_n$, wherein:

V is a tumor-targeting molecule that may be optionally contain a moiety inserted between V and D. The tumor targeting molecule can be any molecule capable recognizing or binding to a specific area of the body. Non-limiting examples of tumor-targeting molecules include biotin, antibodies, fragments of antibodies, monoclonal antibodies, a protein, a peptide, oligopeptides, aptamers, hyaluronic acid, lectin, a saccharide, a hormone, polyunsaturated fatty acids, folic acid, transferrin or a neurotransmitter. Non-limiting examples of moieties that may be inserted between V and D include polyamino acid, such as polyglycine, polylysine, polytyrosine and polyphenylalanine, dextran, polysaccharides, polypropylene oxide (PPO), poly D-amino acids, a copolymer PEG with PPO, PEG, polyglycolic acid, polyvinyl pyrolidone, polylactic acid and polyvinylalcohol or a mixture thereof. m and n are the same or different and can be 1 to 64.

D is a half-dendron. Non-limiting examples of half-dendrons of dendrimers include those of PAMAM (poly(amidoamine)), PAMAMOS (poly(amidoamine-organosilicon)dendrimers), PPI (poly(propylene imine)), amphiphilic dendrimer, chiral dendrimer, multilingual dendrimer, micellar dendrimer, Tecto dendrimer and Frechet type dendrimer.

C is any cleavable functionality that may optionally contain a spacer moiety. Non-limiting examples of cleavable functionalities include 2,2'-dithiobis(ethylamine (cystamine) and its analogs such as 3,3'-dithiobis(propylamine) and 4,4'-dithiobis(butylamine). Non-limiting examples of optional spacer moieties include PEGylated bis-maleimido, carbamates, thiocarbamates, carbonate groups, thiocarbonate groups, ureas, thioureashydrazones, cis-aconityls, bifunctional peptides and bis-bromo compounds.

D' is a half-dendron. Preferably D' is a half-dendron that differs from a half-dendron D, in either differing generations and/or differing structure.

T is a cytotoxic agent. Non-limiting examples of cytotoxic agents include paclitaxel, taxoids such as docetaxel, cabazitaxel and SB-T-1214, vinca alkaloids such as vinblastine and vincristine, desacetyl vinblastine and desacetyl vinblastine hydrazine, anthracyclines such as doxorubicin, daunorubicin, morpholino-doxorubicin and cyanomorpholino-doxorubicin, geldanamycin, ricin, abrin, diphtheria toxin, modecin, tetanus toxin, mycotoxins, mellitin, α-amanitin, pokeweed antiviral protein, ribosome inhibiting proteins, auristatin E, auristatin EB (AEB), auristatin EFP (AEFP), monomethyl auristatin E (MMAE), 5-benzoylvaleric acid-AE ester (AEVB), tubulysins, disorazole, epothilones, SN-38, topotecan, rhizoxin, duocarmycin, actinomycin, ansamitocin-P3, duocarmycin, duocarmycin B2, maytansine, maytenisinoids (DM1, DM2, DM3, DM4), calicheamicin, echinomycin, colchicine, estramustine, cemadotin, eleutherobin, 1-hydroxyauramycin A, aclacinomycin, abafilomycin C1, dinaktin, dolastatin such as dolestatin-10, combretastatin, leptomycin B, pluramycins, staurosporine, nogalamycin, rhodomycins, mithramycin, rabelomycin, rapamycin, alnumycin, chartreusin, geliomycin, gilvocarcin, piericidin, chlorambucil, cyclophosphamide, melphalan, and antimetabolites such as methotrexate, dichlorormethatrexate, methopterin, cytosine arabinoside, leurosine, leurosideine, mitomycin C, mitomycin A, carminomycin, aminopterin, tallysomycin, podophyllotoxin, camptothecin.

F is optionally a fluorescent tagging molecule. Non-limiting examples of fluorescent tagging molecules include fluorescein and its derivatvies, rhodamine and its derivatives, coumarin and its derivatives, boron dipyrromethane (BODIPY) fluorophore derivatives, naphthalimide derivatives (Lucifer Yellow), maleimide and its derivatives, and/or radionuclides such as, but not limited to, radiohalides or a metal chelator carrying radionuclide.

The tumor-targeting molecule can be a biotin, a protein, a vitamin, a peptide, lectin, a saccharide, or other moiety that selectively binds or interacts with the cell surface of a tumor or another part of the tumor. Some types of molecules on the surface of a cell that may be targeted by a specific tumor-targeting molecule include receptors, oligosaccharides, lectins, adhesion molecules, proteoglycams, integrins, immunoglobulins, major histocompatibility complex, human leukocyte antigen and glycoproteins. Non-limiting examples of receptors include tyrosine kinase receptors, such as vascular endothelial growth factor (VEGF) receptor, and epidermal growth factor (EGF) receptors, such as HER-1, HER-2, HER-3 and HER-4. In a preferred embodiment, the tumor-targeting molecule is biotin.

The tumor-targeting molecule can also be, for example, a receptor-specific ligand. A receptor-specific ligand is a natural or synthetic molecule, such as a hormone or neurotransmitter, which specifically binds to a receptor on the surface of a cell. Non-limiting examples of receptor-specific ligands include bombesin, transferrin, VEGF and EGF.

In another embodiment, the tumor-targeting molecule can be a molecule that comprises the hypervariable region (CDR) of an antibody and has binding characteristics that are the same as, or comparable to, those of the whole antibody. The tumor-targeting molecule can be a fragment of an antibody or a monoclonal antibody.

Suitable fragments of antibodies include any fragment that comprises a sufficient portion of the hypervariable region to bind specifically, and with sufficient affinity, to a molecule on the surface of a cell. Such fragments can, for example, contain one or both Fab fragments, or the F(ab')$_2$ fragment. The antibody fragments can contain all six complementarity-determining regions of the whole antibody, although functional fragments containing fewer than all such regions, such as three, four or five CDRs, may also be suitable.

The preferred fragments are single chain antibodies, or Fv fragments. Single chain antibodies are polypeptides that comprise at least the variable region of the heavy chain of the antibody linked to the variable region of the light chain, with or without an interconnecting linker. These chains can be produced in bacteria or in eukaryotic cells.

The antibodies and functional equivalents can be members of any class of immunoglobulins, such as: IgG, IgM, IgA, IgD, or IgE, and the subclasses thereof. The preferred antibodies are members of the IgG1 subclass. The functional equivalents may also be equivalents of combinations of any of the above classes and subclasses.

Suitable variable and hypervariable regions of antibodies may be derived from antibodies produced by any mammal in which monoclonal antibodies are made. Non-limiting examples of suitable mammals include rabbits, rats, mice, horses, goats and primates. Preferably, the monoclonal antibodies are derived from mice or rats. The monoclonal antibodies thus obtained are humanized by methods known in the art for the purpose of human clinical use.

Dendrimers are a class of polymers which are also known as starburst polymers because of their shapes (see FIG. 1). In general, a dendrimer exhibits a tree-like molecular architecture with an interior core, interior layers (also called "generations") which consist of repeating units regularly attached to the core, and an exterior surface of functional terminal groups attached to the outermost generation. Generation Number (usually abbreviated to G#) is determined by the number of focal points going from the core towards the surface. The molecular weight of the dendrimer itself and the number of terminal functional groups can easily be determined by the generation.

The dendrimeric structure can have from 4 to 384 branches by forming expanding monomer layers, such as having 4, 8, 16, 32, 64, 128 or 256 branches or 6, 12, 24, 48, 96, 192 or 384 branches, wherein each 4 or 6 branches defines a first layer or generation, 8 or 12 branches a second layer or generation, etc. The dendremeric structure can have molecular weight from about 600 to 60,000 Da, such as about 3,000, 7,000, 14,000, 29,000 or 59,000 and may be in the form of a star like symmetrical structure.

The dendrimeric structure can comprise linear polymer structures as well as branched polymer structures. The linear polymer, which is attached to said dendrimer, may be selected from the group consisting of polyamino acid, such as polyglycine, polylysine, polytyrosine and polyphenylalanine, dextran, polysaccharides, polypropylene oxide (PPO), poly D-amino acids, a copolymer of PEG with PPO, PEG, polyglycolic acid, polyvinyl pyrolidone, polylactic acid and polyvinylalcohol or a mixture thereof. The linear polymer structures are therefore, in one embodiment of the present invention, hydrophilic. A hydrophilic polymer structure provides the macromolecule with increased water solubility. Such a hydrophilic polymer structure may also counteract the decreased water solubility, which hydrophobic cytotoxic agents may contribute to. Further, a hydrophilic polymer may prevent hydrophobic cytotoxic agents on the same macromolecule conjugate from aggregating, or at least reduce such aggregation. The length of said linear polymer may be about 3 to about 20 atoms, i.e., the backbone atoms in the linear polymer, such as 3, 4, 5, 6, 8, 10, 15, or 20 atoms. The group linking the linear polymers to said dendrimeric structure may be selected from the group consisting of amides, carboxylic acid esters, thioesters, disulfides, thiourethanes, carbamates, carbonates, thioureas or ureas.

Non-limiting examples of dendrimers of the present disclosure include PAMAM (poly(amidoamine)), PAMAMOS (poly(amidoamine-organosilicon)), DAB (diaminobutane-poly(propylene imino). PPI (poly(propylene imine)), amphiphilic dendrimer, chiral dendrimer, multilingual dendrimer, micellar dendrimer, Tecto dendrimer and Frechet type dendrimer. In a preferred embodiment of the present disclosure, PAMAM is the dendrimer of the conjugate.

To solve the problem of irreproducibility of functionalities of dendrimers from batch to batch, a preferred embodiment is a PAMAM dendrimer with a cleavable core (Asymmetric Bow-tie PAMAM Dendrimer-based Conjugates (ABPDCs)). This allows for full functionalization of different functionalities on different generation dendrimers, to be purified and isolated, followed by the cleavage of the fully functionalized dendrimer to generate to half dendrons. Two half-dendrons may then be recoupled, through a linker, to form an asymmetric-based construct. Non-limiting examples of cleavable cores include cystamine, and those described in *Angew. Chem. Int. Ed.*, 2007, 46, 1010-1017 (incorporated herein by reference). In a preferred embodiment, the cleavable core is cystamine.

A spacer moiety may also be employed between the two half dendrimers. Non-limiting examples of spacers include PEGylated bis-maleimido, carbamates, thiocarbamates, carbonate groups, thiocarbonate groups, ureas, thioureashydrazones, cis-aconityls, bifunctional peptides and bis-bromo compounds.

The cytotoxic agent may be a natural or synthetic agent acting at different mechanisms such as inhibiting DNA or RNA synthesis, inhibiting protein synthesis or interating with tubulin, topoisomease inhibitors, ionophores, and interaction with heat shock proteins and may come from various natural sources, such as, bacteria, yeasts, plants or animals.

The cytotoxic agent can be selected from paclitaxel, taxoids such as docetaxel, cabazitaxel and SB-T-1214, vinca alkaloids such as vinblastine and vincristine, desacetyl vinblastine and desacetyl vinblastine hydrazine, anthracyclines such as doxorubicin, daunorubicin, morpholino-doxorubicin and cyanomorpholino-doxorubicin, geldanamycin, ricin, abrin, diphtheria toxin, modecin, tetanus toxin, mycotoxins, mellitin, α-amanitin, pokeweed antiviral protein, ribosome inhibiting proteins, auristatin E, auristatin EB (AEB), auristatin EFP (AEFP), monomethyl auristatin E (MMAE), 5-benzoylvaleric acid-AE ester (AEVB), tubulysins, disorazole, epothilones, SN-38, topotecan, rhizoxin, duocarmycin, actinomycin, ansamitocin-P3, duocarmycin, duocarmycin B2, maytansine, maytensinoids (DM1, DM2, DM3, DM4), calicheamicin, echinomycin, colchicine, estramustine, cemadotin, eleutherobin, 1-hydroxyauramycin A, aclacinomycin, abafilomycin C1, dinaktin, dolastatin such as dolestatin-10, combretastatin, leptomycin B, pluramycins, staurosporine, nogalamycin, rhodomycins, mithramycin, rabelomycin, rapamycin, alnumycin, chartreusin, geliomycin, gilvocarcin, piericidin, chlorambucil, cyclophosphamide, melphalan, and antimetabolites such as methotrexate, dichlorormethatrexate, methopterin, cytosine arabinoside, leurosine, leurosideine, mitomycin C, mitomycin A, carminomycin, aminopterin, tallysomycin, podophyllotoxin, camptothecin. However, other known drugs may be modified in order to provide a functional group for conjugation to the linker described herein. Such chemical modification is known in the art. In a preferred embodiment, the cytotoxic agent is a taxoid. In a more preferred embodiment, the cytotoxic agent is SB-T-1214.

The conjugates of the present disclosure are either uncharged or in the form of pharmaceutically acceptable salts. The term "pharmaceutically acceptable salt" refers to a salt prepared from the conjugate and, for example, an acid or a base. The salt is acceptably non-toxic and has acceptable pharmacokinetics.

Such salts are formed by well known procedures. Suitable acids for producing salts of the conjugates include mineral acids and organic acids. Non-limiting examples of mineral acids include hydrochloric, hydroiodic, hydrobromic, phosphoric, metaphosphoric, nitric and sulfuric acids. Non-limiting examples of organic acids include tartaric, acetic, citric, malic, benzoic, pyridine, gluconic, gulonic, succinic, arenesulfonic and p-toluenesulfonic acid.

Suitable bases for producing salts of the conjugates include inorganic and organic bases. Non-limiting examples of inorganic bases include hydroxides of lithium, sodium, potassium, magnesium and calcium. Non-limiting examples of organic bases include primary, secondary and tertiary alkyl amines.

For the pharmaceutical purposes described above, the conjugate of the present disclosure can be formulated in pharmaceutical preparations optionally including a suitable pharmaceutical carrier or excipient. In this specification, a pharmaceutical carrier is considered synonymous with a vehicle or an excipient as understood by practitioners in the art. Non-limiting examples of carriers include starch, milk, sugar, certain types of clay, gelatin, stearic acid or salts thereof, talc, vegetable fats or oils, gums and glycols.

The conjugate formulation can also comprise one or more of the following: a stabilizer, a surfactant, a salt, a buffering agent, or a combination thereof. The stabilizer can be, for example, an amino acid, such as glycine; or an oligosaccharide, such as sucrose, tetralose, lactose or a dextran. Alternatively, the stabilizer may be a sugar alcohol, such as mannitol; or a combination thereof.

Non-limiting examples of suitable surfactants include Tween 20, Tween 80, a polyethylene glycol and a polyoxyethylene glycol at from about 0.001% (w/v) to about 10% (w/v). The salt or buffering agent can be any salt or buffering agent, such as, for example, sodium chloride, sodium phosphate or potassium phosphate.

The conjugate formulation can additionally contain one or more conventional additives. Non-limiting examples of such additives include a solubilizer, such as, for example, glycerol; an antioxidant, such as, for example, benzalkonium chloride, benzyl alcohol, chloretone or chlorobutanol; an anesthetic agent, such as, for example, a morphine derivative; an isotonic agent, or a combination thereof. As a precaution against oxidation or other spoilage, the conjugate can be stored under nitrogen or another inert gas in vials sealed with impermeable stoppers.

For aqueous suspensions and solutions, emulsifying agents, suspending agents or combinations thereof can be added. In addition coloring, sweetening and flavoring agents can be added to the formulation. Sterile solutions of the conjugate formulation can also be employed. If required, the pH of the solutions can be suitably adjusted and buffered, the methods of which are well known to a person of skill in the art.

The conjugates can be administered alone or as an adjunct with other conventional drugs for treating conditions or diseases, including cancer. The conjugates may be administered by any method known in the art. Non-limiting examples of suitable modes of administration include oral, systemic, and topical administration.

Liquid or solid oral formulations are well known in the art. Non-limiting examples of formulations suitable for oral administration include tablets, capsules, pills, troches, elixirs, suspensions and syrups.

Systemic administration includes enteral or parenteral modes of administration, e.g., intravenous, intramuscular, subcutaneous or intraperitoneal. For example, the conjugate can be administered by injection of a solution or suspension; or intranasally, in the form of, for example, a nebulizer, liquid mist or intranasal spray; or transdermally, in the form of, for example, a patch; or rectally, in the form of, for example, a suppository; or intrabronchially, in the form of, for example, an inhaler spray.

The timing of the administration of the conjugate formulation can also be modified. For example, the formulation can be administered intermittently or by controlled release. Controlled release administration is a method of drug delivery to achieve a certain level of the drug in the body over a particular period of time.

The disclosure also relates to a kit, system or a method of using said kit or system, comprising the dendrimer-conjugate mentioned and defined above and an extracorporeal device comprising at least tumor-targeting molecule. One example of such an extracorporeal device is Mitra-Dep®. By providing such a kit it is possible to use the kit for the removal of dendrimer-conjugates which have not bound the target in a mammal such as a human, dog, cat, horse, cow, camel or any other animal by introducing said dendrimer-conjugate into the mammal, allowing said dendrimer-conjugate to circulate within said mammal and binding to said target, and finally allowing the body fluid passing the extracorporeal device and allowing binding of free conjugates to said extracorporeal device and thereby enable the removal of the surplus of dendrimer-conjugate from the mammal. By removing the surplus of dendrimer-conjugate from cells and organs within the mammal which the dendrimer-conjugate are not directed against the exposure to these healthy cells and organs will be diminished. Such a device could be a filter (e.g. holofiber filter) or filled with an adsorbent.

The kit or system may also comprise one or more tubings. The tubing set is/are adapted to the extracorporeal device as well as the apparatus to be used to remove the whole blood from the mammal. Examples of such tube sets are the tube set from Fresenius Medical Care AG, D-61346 Bad Hamburg, Del., inlet tubing line "Art" art no: 9798814 and return tubing line, art no: 979521-1.

To facilitate the extracorporeal depletion an apparatus for extracorporeal circulation of whole blood or plasma will be connected to the patient through tubing lines and blood access device(s). Such an apparatus should provide conduits for transporting the blood to an adsorption device and conduits for returning the processed blood or plasma to the patient. In the case plasma is processed through the adsorption device, a plasma separation device is needed as well as means of mixing the concentrated blood with processed plasma. The later is normally achieved by leading the two components into an air-trap where the mixing occurs. Any person skilled in the art of extracorporeal technology would be familiar with the wide range of equipment and disposables available for that purpose.

In the case where whole blood is processed, an ordinary dialysis machine can constitute the base for such an apparatus. Dialysis machines are normally equipped with all the necessary safeguards and monitoring devices to meet patient safety requirements and allow easy handling of the system. Hence, in a one embodiment whole blood is processed and a standard dialysis machine is utilized with only minor modifications of the hardware. However, such a machine requires a new program fitted to the new intended purpose.

Blood access could be achieved through peripheral vein catheters, or if higher blood flow is needed, through central vein catheters such as, but not limited to, subclavian or femoral catheters.

The compounds of the present disclosure show highly selective activity towards the ID-8 murine and human ovarian cancer cell lines and the MX-1 human breast carcinoma cell line, which over-express biotin receptors, using the WI-38 human lung fibroblast cell line as the negative control. Thus, these compounds are highly selective and efficacious against cancer cell lines, over-expressing biotin receptors such as human breast cancer cell lines, MCF7, BT-20, LCC6-WT, MDA-MB 231, and SkBr3, human colon cancer cell lines, HCT116, HT-29 and DLD-1, and human prostate cancer cell lines, PPT2 and PC3MM2.

The dendrimer-based conjugate can be administered to a subject in need thereof in the amount of from 0.1 mg/Kg-200 mg/Kg of body weight. The dendrimer-based conjugate can be administered in an amount of at least, above, up to, or less than, for example, 0.1, 0.2, 0.5, 1.0, 2.0, 5.0, 10.0, 50.0, 100.0, 150.0 and 200.0 mg/Kg of body weight.

Examples have been set forth below for the purpose of illustration. However, the scope of this disclosure is not to be in any way limited by the examples set forth herein.

Example 1

Modification of PEG Trimer and Tetramer (Scheme 1)

To 15 grams of polyethene glycol (n=3) was added 0.45 eq of tert-butyl acrylate and 1 mol % potassium tert-butoxide in THF at 0° C. to room temperature for 3 days to yield compound 1. Compound 1 was added to 1.2 eq of methanesulfonyl chloride, 1.2 eq of triethyl amine in THF at 0° C. to room temperature for 3 hours. The pH was adjusted to 8 and 1.2 eq of sodium azide was added in water. The reaction was refluxed overnight to yield compound 2. To compound 2 was added 3 eq of triphenylphosphine in a THF:water ratio of 7:2 at room temperature for 18 hours to afford compound 3.

To 10 grams of polyethene glycol (n=4) was added 2.5 eq of methanesulfonyl chloride, 2.5 eq of triethyl amine in THF at 0° C. to room temperature for 4 hours. The pH was adjusted to 8 and 2.5 eq of sodium azide was added in water. The reaction was refluxed for 19 hours to yield compound 4. To compound 4 was added 0.9 eq of triphenylphosphine and 0.65 M phosphoric acid in diethyl ether at room temperature for 22 hours to afford compound 5.

Scheme 1

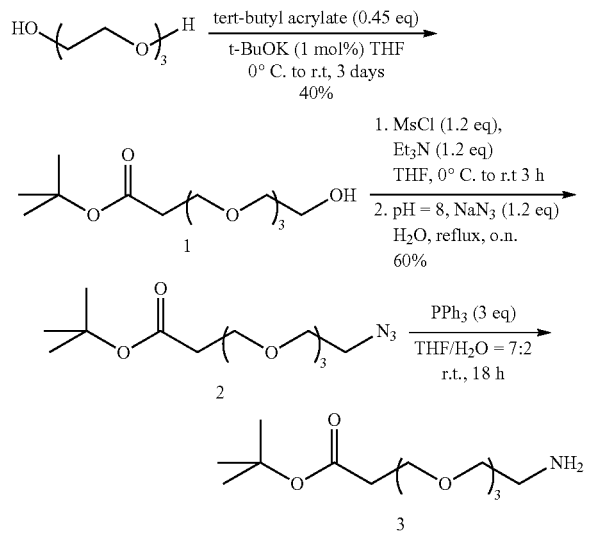

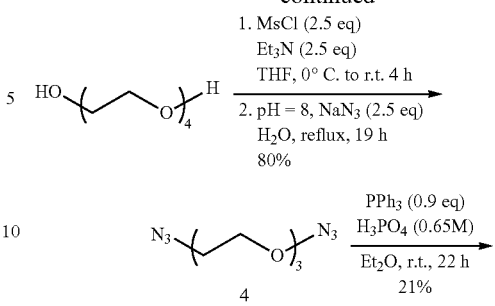

Example 2

Biotinylated PEGylated G3 PAMAM Dendrimer (Scheme 2)

To 2 grams of biotin was added 2 eq of N,N'-diisopropylcarbodiimide and 3 eq of N-hydroxysuccinimide in 0.2 M DMF at 45° C. to yield compound 6. One eq of t-Boc protected PEG amine (3) was then added in methylene chloride at room temperature to give compound 7 and deprotected using TFA to afford compound 8, followed be activation using 2 eq of N,N'-diisopropylcarbodiimide and 3 eq of N-hydroxysuccinimide to form its activated ester, compound 9. G3 dendrimer DNT-296 was added to compound 9 in methanol at room temperature to yield compound 10.

Scheme 2

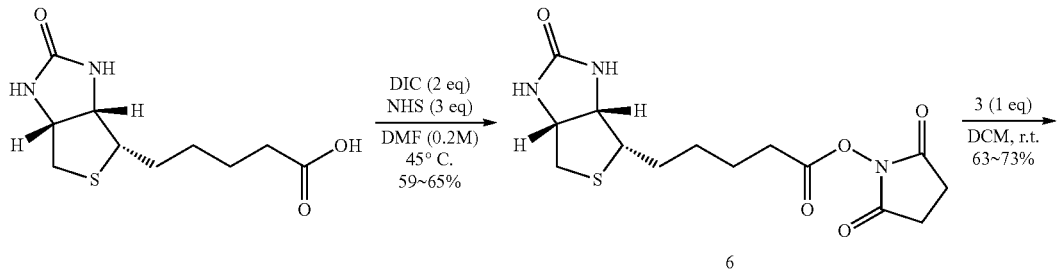

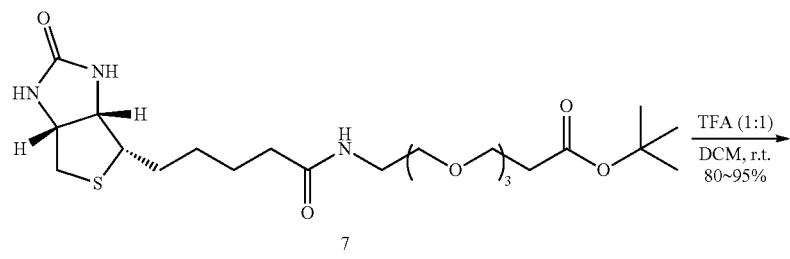

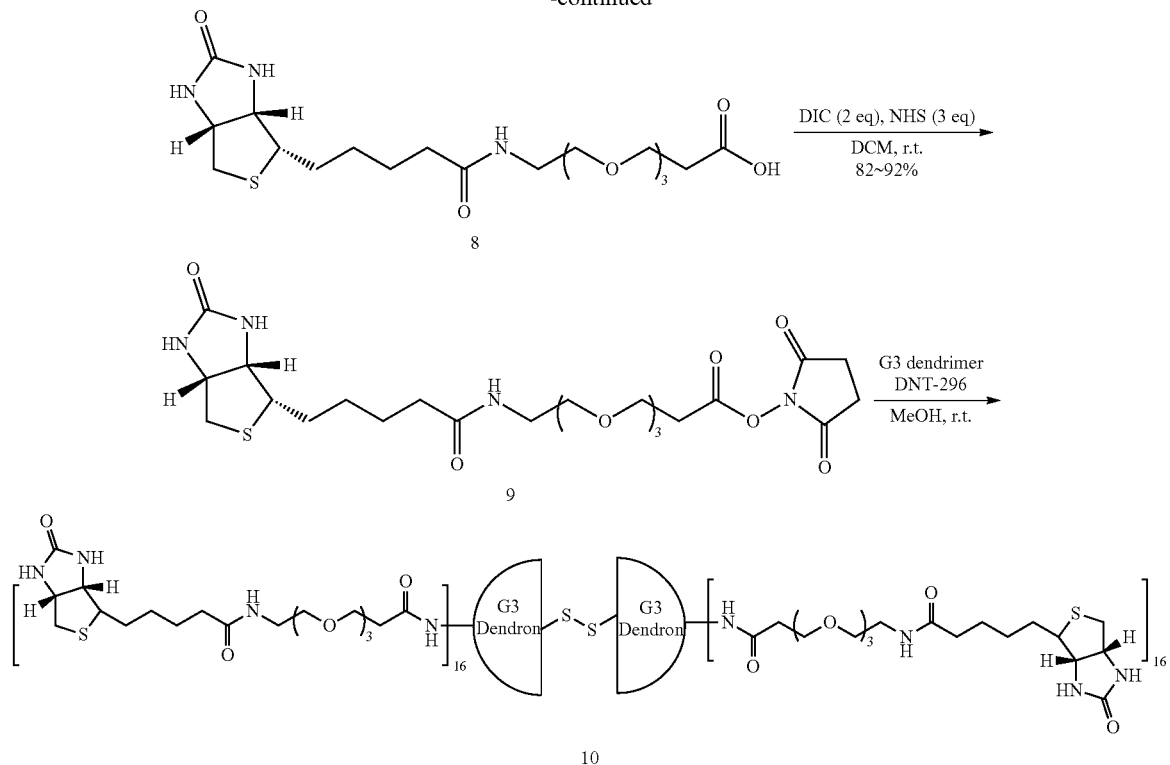

Example 3

"Click-Ready" PEGylated G1 PAMAM Dendrimer (Scheme 3)

4-pentynoic acid was treated with t-Boc protected PEG amine (3) to give compound 11 and deprotected using TFA to afford compound 12, followed by activation using NHS to form its activated ester compound 13. The dendrimer was fully functionalized by amidation of a generation 1 dendrimer bearing a cleavable cystamine core (DNT-294, from Dendritic Nanotechnologies, Inc.) to generate compound 14 leaving a terminal alkyne for orthoganol conjugation through a click reaction. Compound 14 was isolated by preparative HPLC. The purity of 14 was confirmed by LC/MS deconvolution and MALDI analysis.

Scheme 3

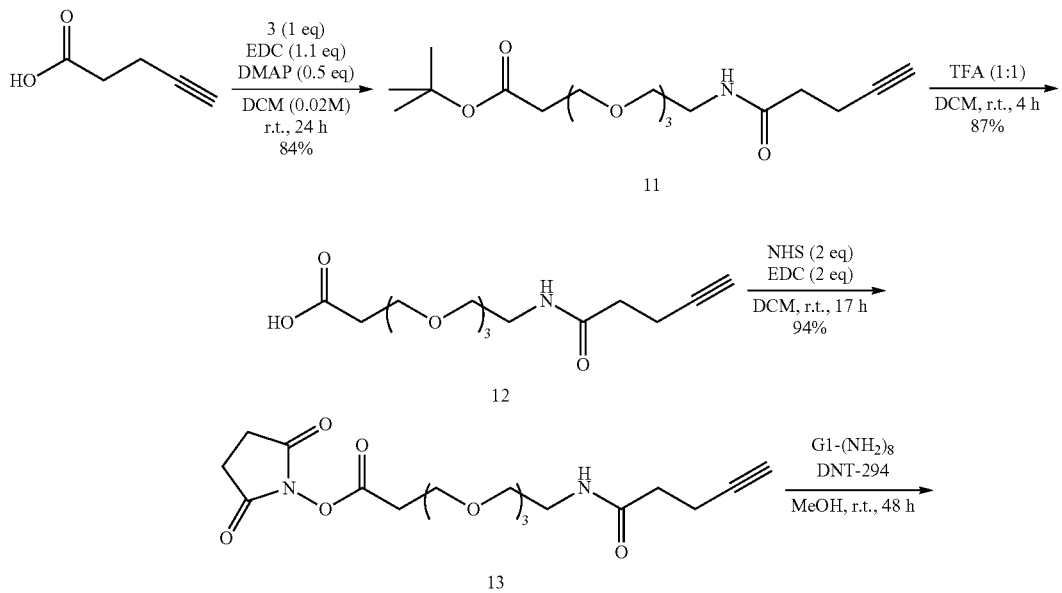

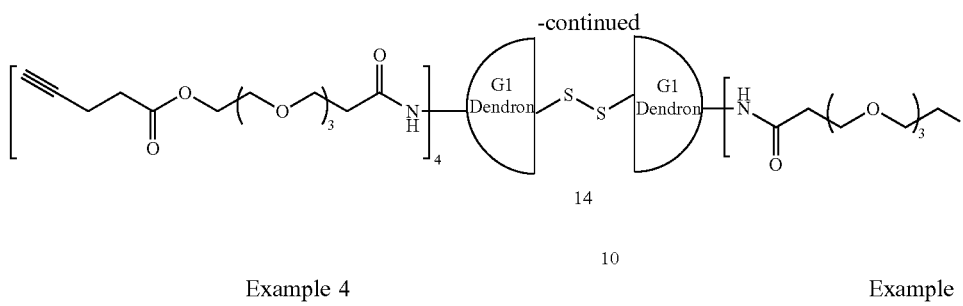

14

10

Example 4

Bis(Maleicimido) PEGylated Linker (Scheme 4)

A 1,4-Michael addition was applied to stepwise couple the fully functionalized generation 1 and generation 3 half dendrons to a bis(maleicimido) linker. 6-Aminocaproic acid was treated with maleic anhydride in acetic acid to generate the ring-open product 15, followed by heating to reflux to form the cyclic condensation product 16. Then in the presence of N-methylmorpholine, the carboxylic acid group of 16 was activated by ethyl chloroformate to yield 17. To increase the solubility of the linker, and the length of the linker so that the first half dendron on the linker will not embed it and prevent a second Michael addition reaction from occurring, 4,7,10-trioxa-1,13-tridecanediamine was added to couple 2 eq of compound 16.

Example 5

"Click-Ready" Dendrimer Scaffold (Scheme 5)

Fully functionalized G1 dendrimer 14 and G3 dendrimer 10 were cleaved to form two half dendrons, and then re-coupled through the bis(maleimido) linker 18 in a stepwise manner. 14 was first selected to be coupled with 18 instead of 10 because 14 exhibits better solubility than 10 so purification with preparative HPLC was feasible and the molecular weight difference was significant from 19 to 20 due to the dominant contribution of 10 so that dialysis as the most applicable purification method could be carried out here for 20.

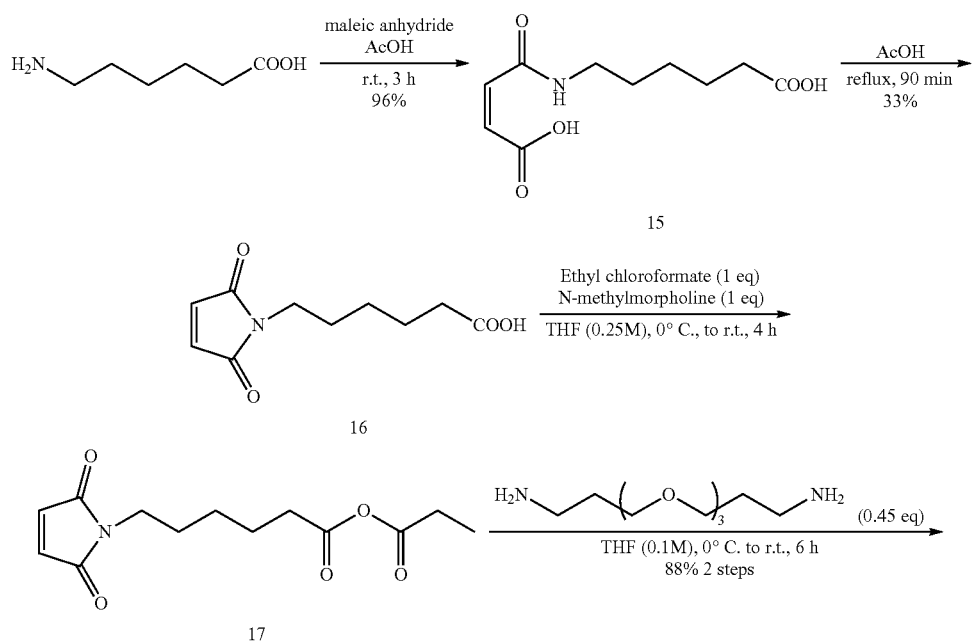

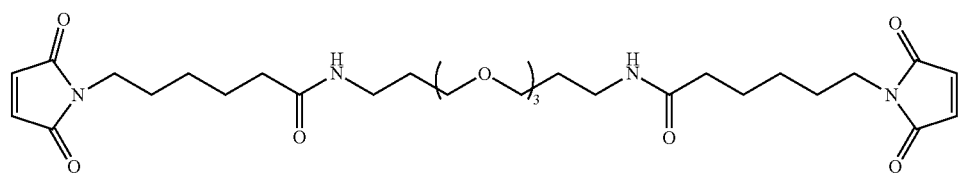

18

Scheme 5
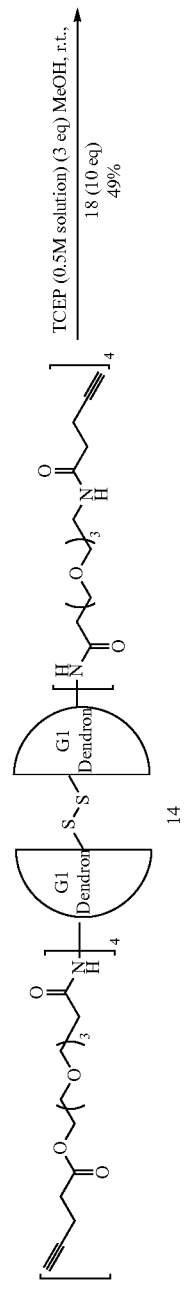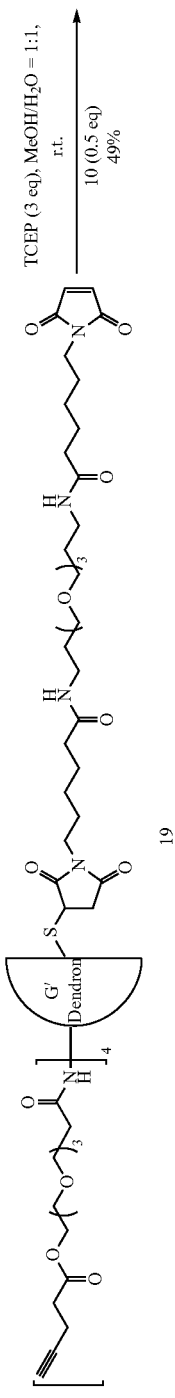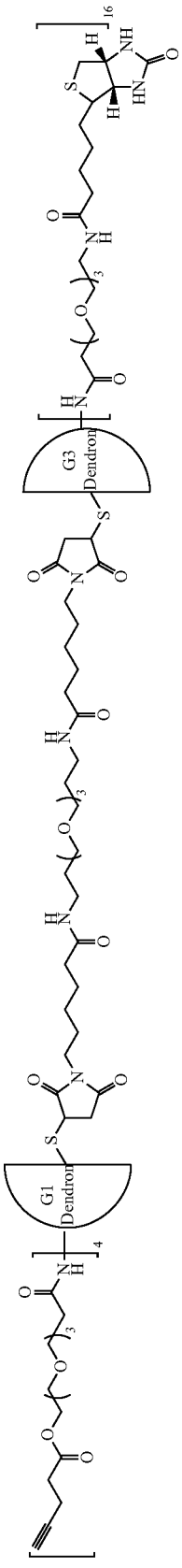

Example 6

Asymmetric Bow-Tie PAMAM-Based Dendrimer (ABTD) Conjugates (Schemes 6 and 7)

To visualize the internalization of ABTD conjugates, a fluorescent probe bearing a PEGylated clickable azido group was derived from commercially available fluorescein. (Scheme 6) Next, the hydroxyl group of C2' position on taxoid SB-T-1214 was first protected with tert-butyldimethylsilyl (TBS) ether to generate 26, followed by EDC coupling with 24 to give 27. Deprotection was performed with HF/pyridine condition to afford drug-fluorescent probe 28.

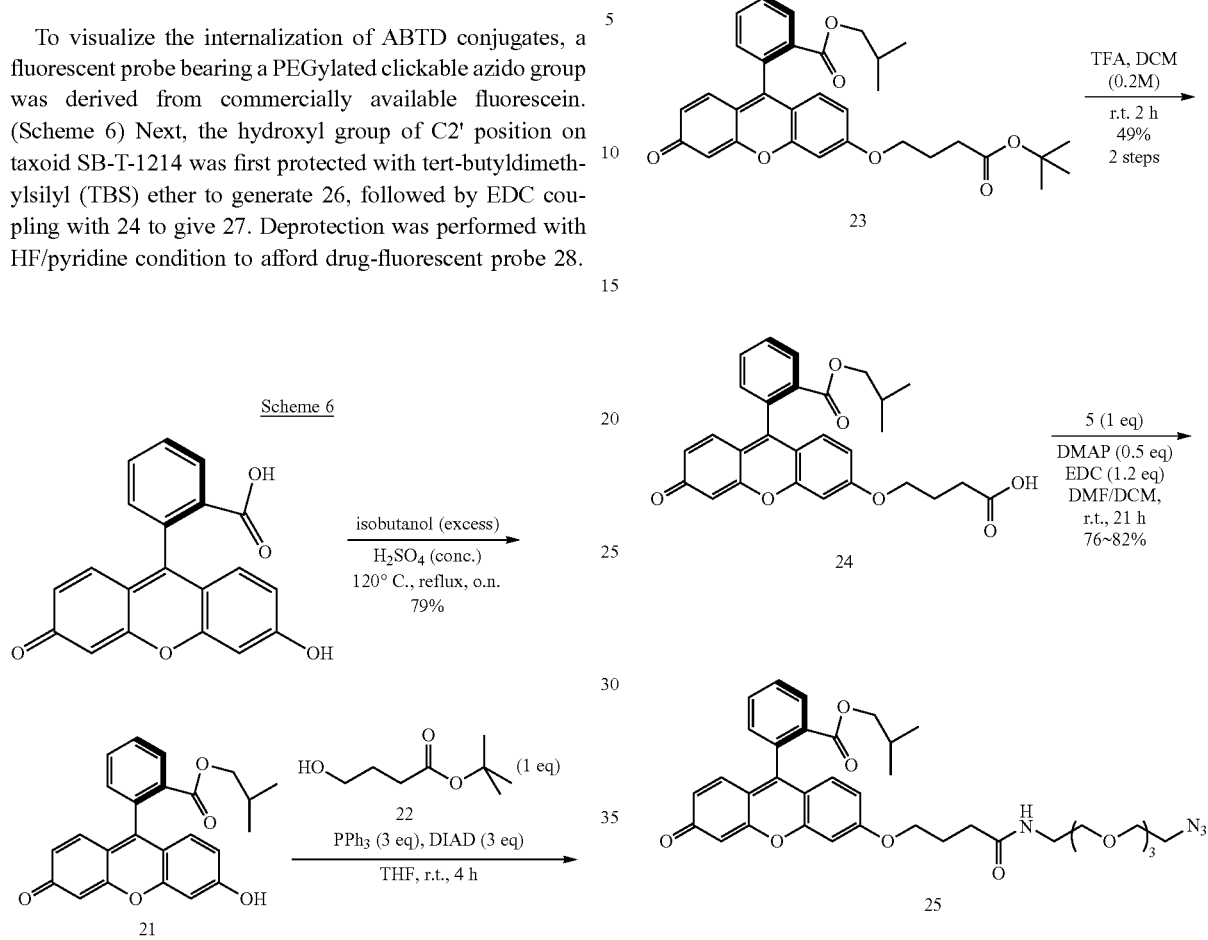

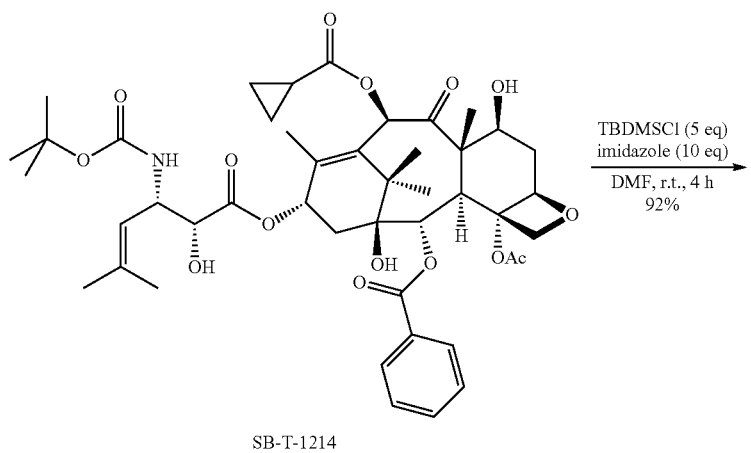

SB-T-1214

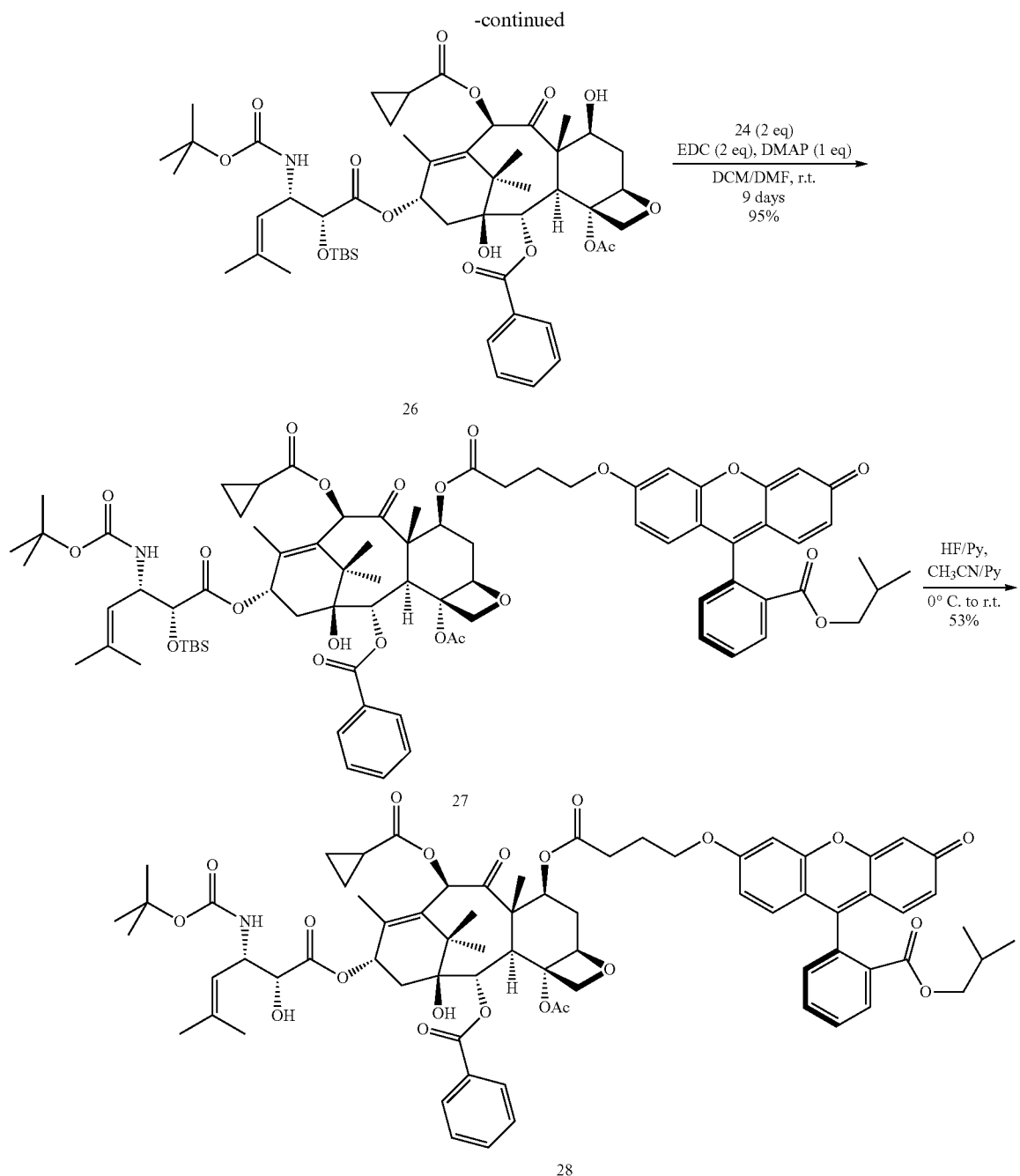

Example 7

Second-Generation Self-Immolative Disulfide Linkers (Scheme 8)

To connect the drug probe (SB-T-1214) and drug-fluorescent probe 28 with the dendrimer scaffold, a linker is critical important since it should be stable during the blood circulation but readily cleavable in tumor to release the drug as its original form. Upon internalization, the intracellular thiol-triggered cascade drug release should generate the original anticancer agent via thiolactone formation and ester bond cleavage.

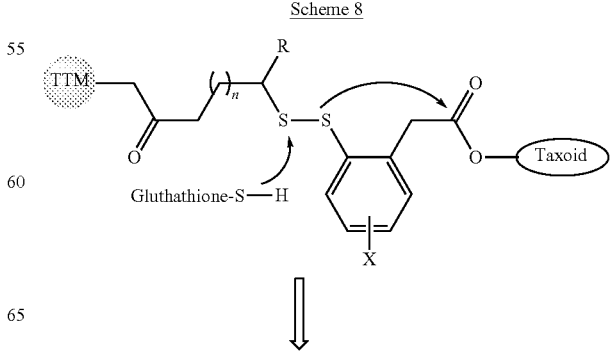

Scheme 8

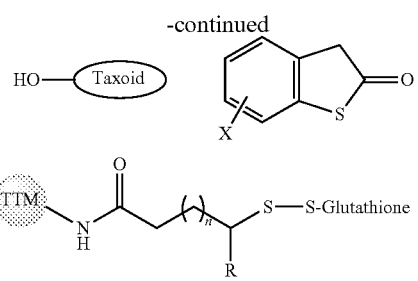

Example 8

Synthesis Diagram of "Click-Ready PEGylated Linker-Drug Probe and Linker Drug Fluorescent Probe (Scheme 9)

SB-T-1214 and SB-T-1214-fluorescein 28 were coupled to disulfide linker 29 under EDC coupling reaction conditions, then after HF/Pyridine deprotection and reactivation of the carboxylic acid, previously made compound 5 was treated to give "click-ready" PEGylated Linker-SB-T-1214 probe 36 and Linker-SB-T-1214-fluorescent probe 37.

Scheme 9

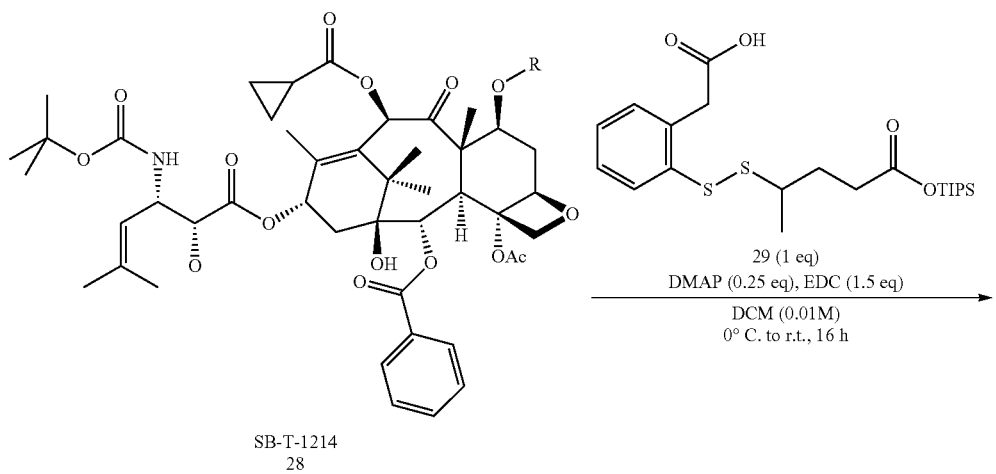

SB-T-1214
28
R = H
R = fluorescein-spacer

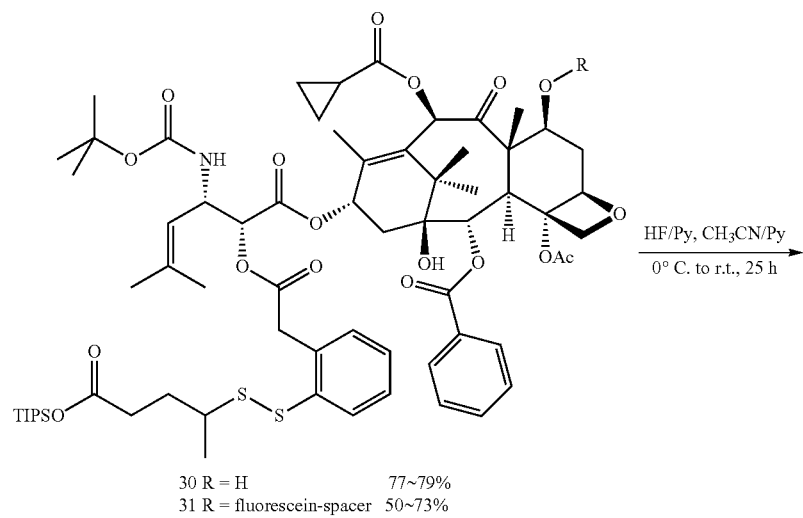

30 R = H             77~79%
31 R = fluorescein-spacer   50~73%

-continued
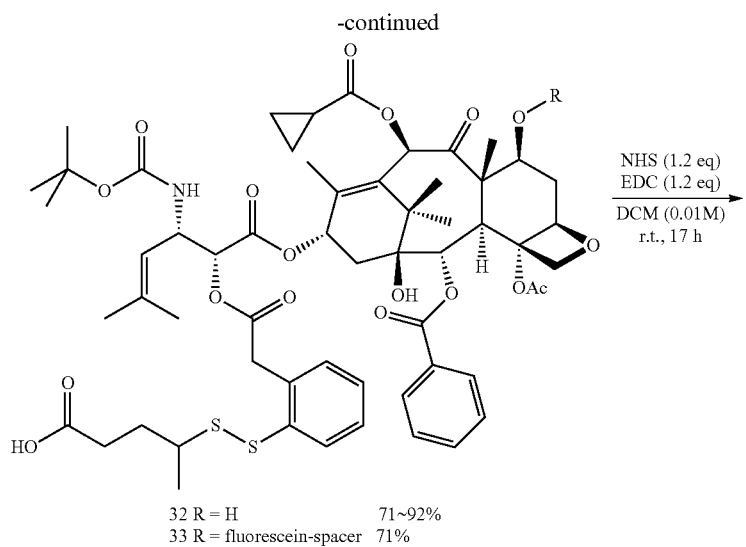
32 R = H  71~92%
33 R = fluorescein-spacer  71%
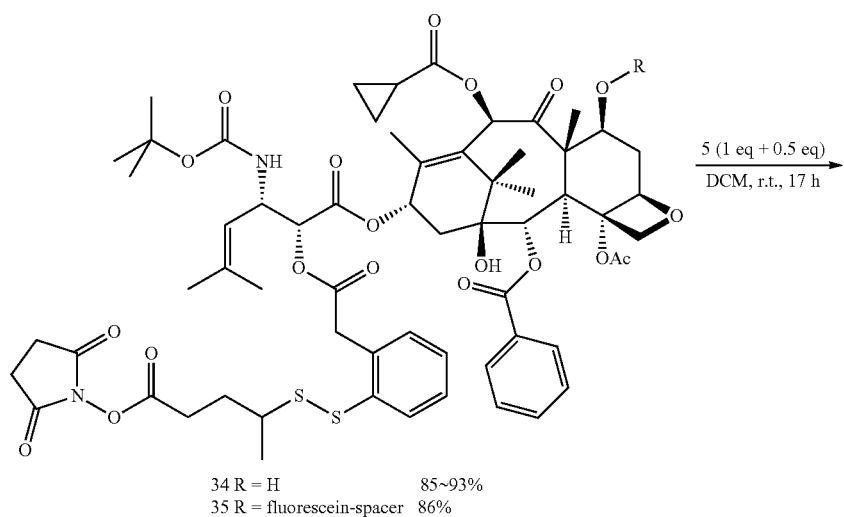
34 R = H  85~93%
35 R = fluorescein-spacer  86%
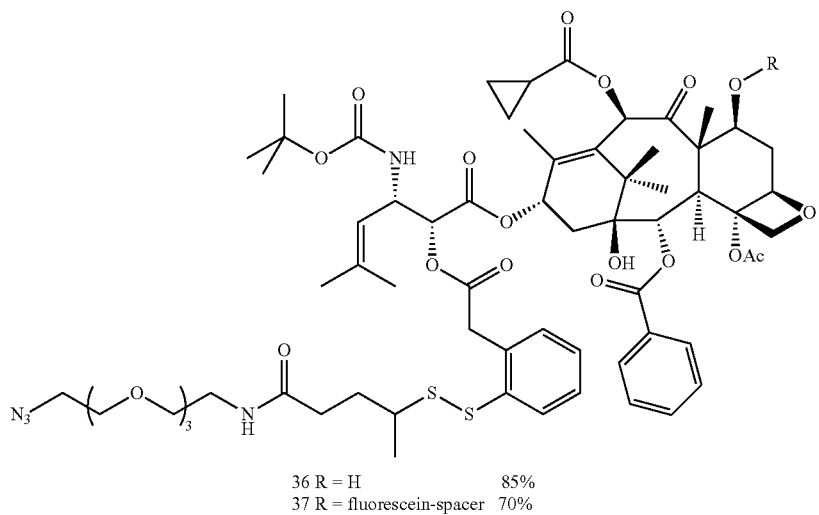
36 R = H  85%
37 R = fluorescein-spacer  70%

Example 9

Synthesis of Asymmetric Bow-Tie PAMAM-Based Dendrimer (ABTD) Conjugates (Scheme 10)

Asymmetric Bow-tie PAMAM-based dendrimer (ABTD) conjugates were constructed under CuACC condition and purified by dialysis with tubing membrane.

Scheme 10
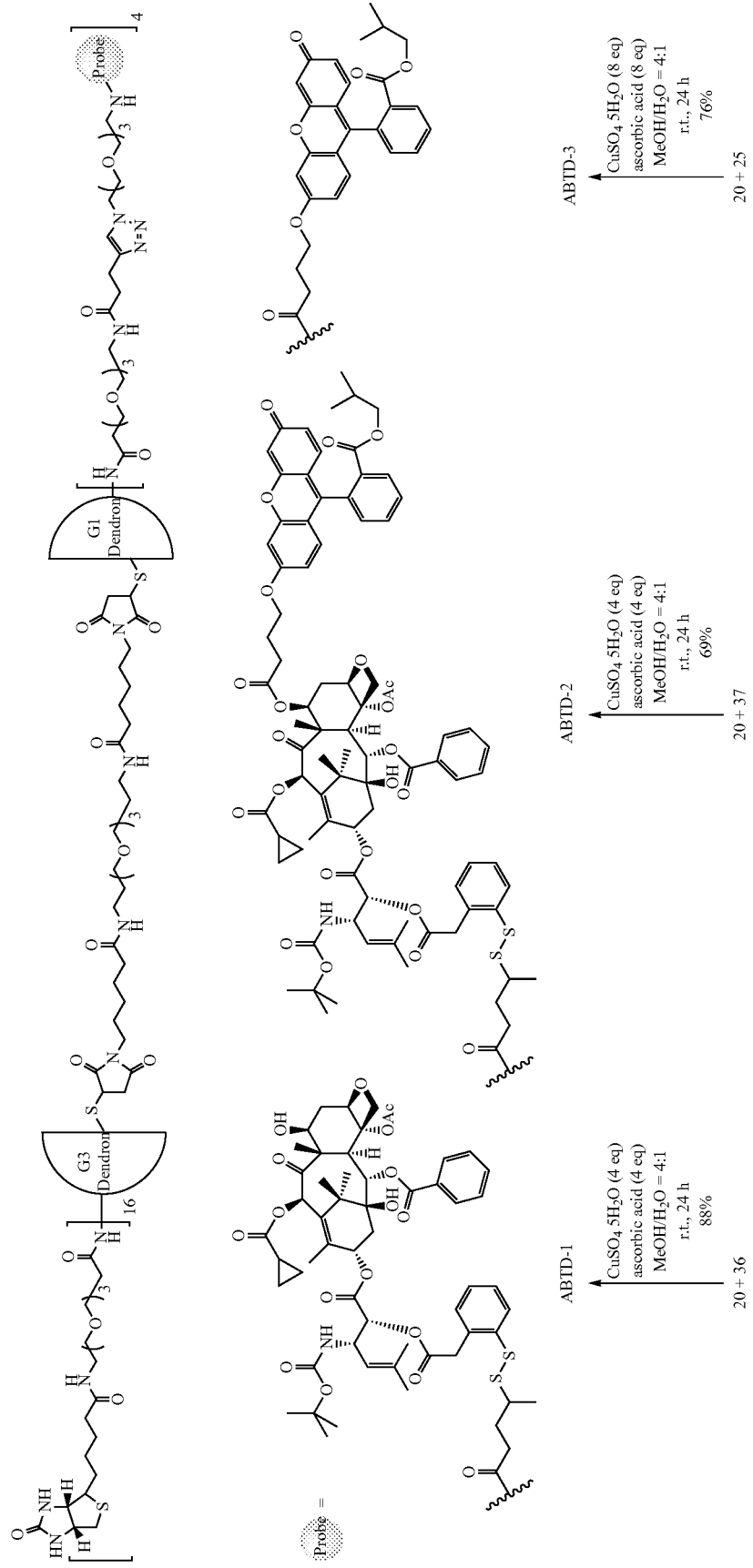

Example 10
Synthesis of SB-T-1214 Linked to PEGylated Biotin (Scheme 11)
Scheme 11
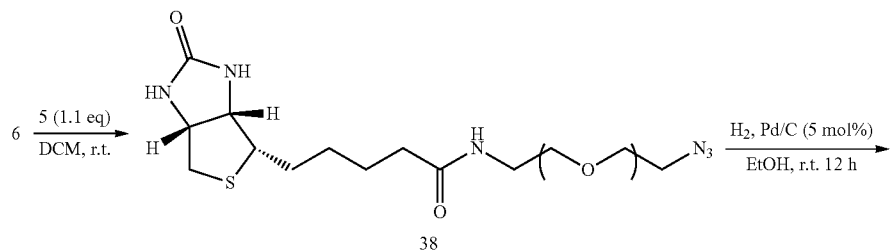
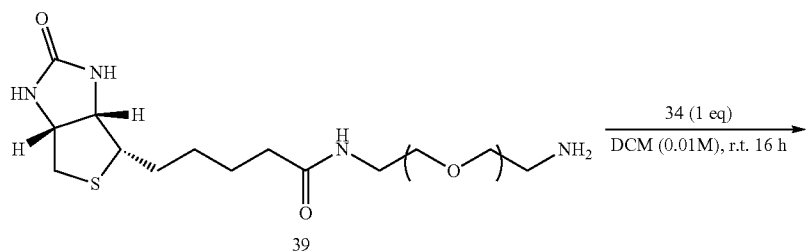
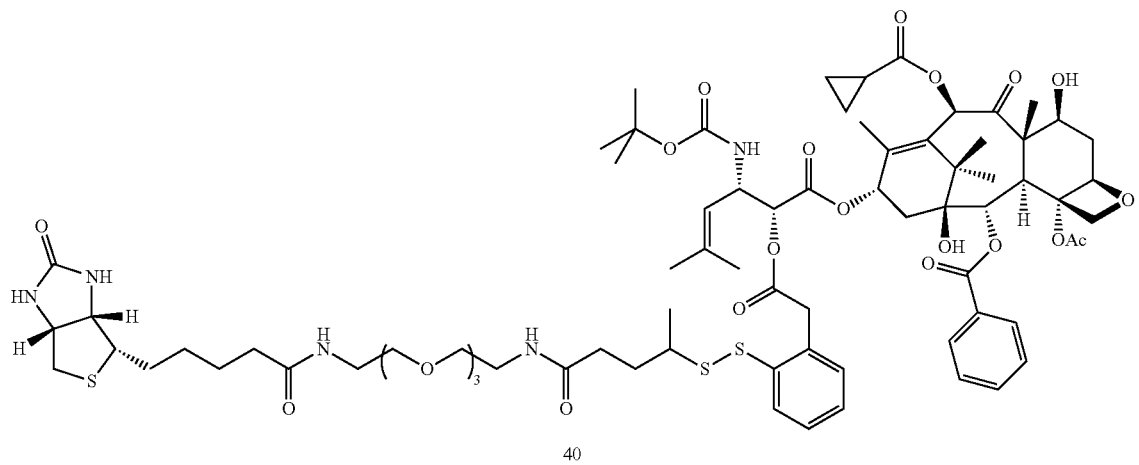

Example 11

Synthesis of PEGylated Biotin-Fluorescent Probe
(Scheme 12)

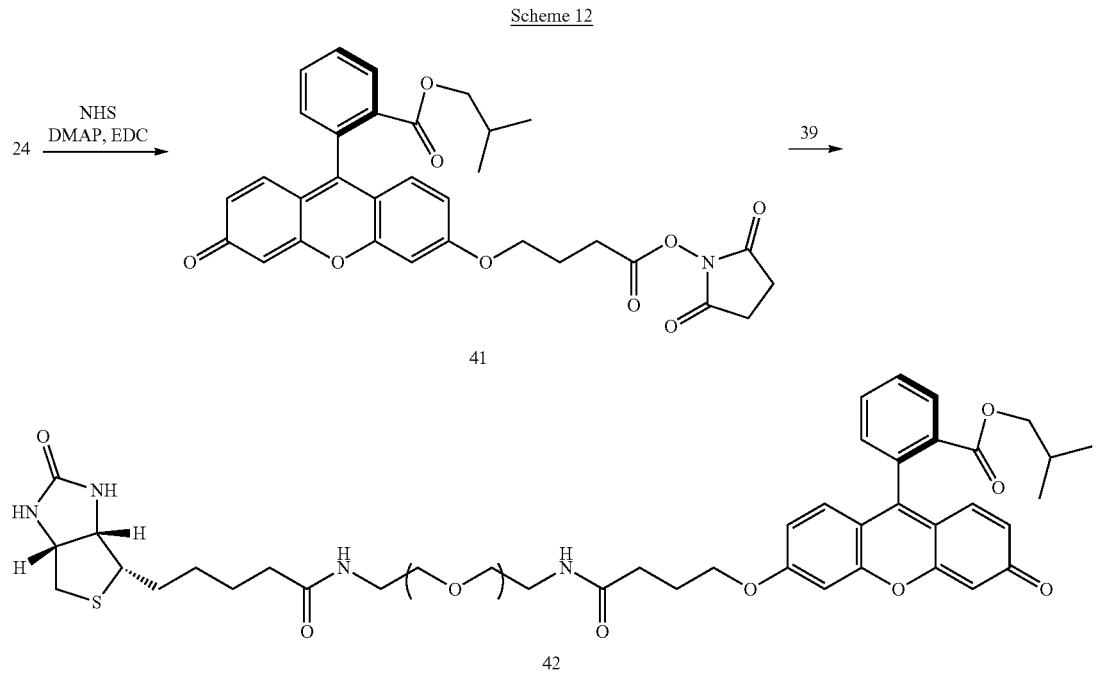

Example 12

Although not bound by any theory, the invention is believed to work as follows. The multiple TTM (16 biotin modules in this case) on a single ABTD macromolecular drug conjugate are expected to increase its targeting ability and affinity to get internalized through Receptor-Mediated Endocytosis (RME) via multi-binding to the biotin receptors, which are overexpressed on the cancer cell surfaces.

Figure 4:
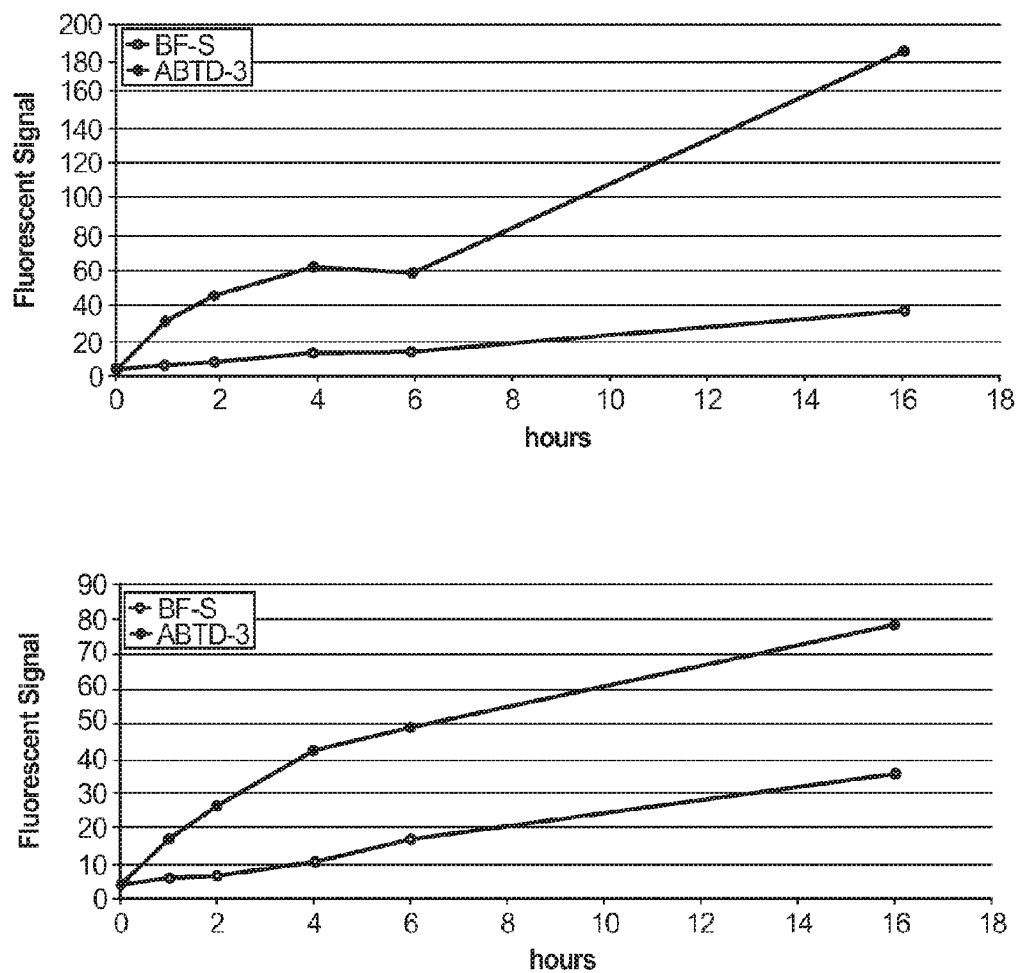
FIG. 4. Time dependent RME rate comparison between a small fluorescent probe (BF-S-biotin-PEG$_3$-Fluorescein) and ABTD-3. Curves were drawn based on the flow cytometry results by incubation of ABTD-3 at the concentration of 10 μM at 37° C. for 0 h, 1 h, 2 h, 4 h, 6 h, and 16 h, in ID-8 (top) and MX-1 (bottom), respectively.

FIG. 4 clearly demonstrates that at 10 μM concentration of probes, with an increase in incubation time, BF-S and ABTD-3 both can be internalized via RME against two different cancer cell lines (ID-8 and MX-1) overexpressing biotin receptors. At the initial stage the RME rate of ABTD is higher than BF-S, which indicates the multiple TTM can increase the targeting ability and affinity to the cancer cells. In addition, for each time point, in terms of the different number of inherited fluorescein of ABTD-3 and BF-S, the fluorescein signal intensity of ABTD-3 is more than 4 times of BF-S against ID-8 cell line, suggesting that the multiple TTM can enhance the cell uptake of the whole conjugate via RME, resulting in more probes internalized at the end.

Example 13

FIG. 5 clearly showed the efficient internalization of ABTD-3 via RME using CFM. Flow cytometry also indicates that at 20 μM concentration, the internalization of ABTD-3 reaches saturation since the fluorescein signal intensity slightly increases from 1 hour to 3 hours incubation period.

Example 14

TABLE 1

Cytotoxicity ($IC_{50}$, nM) of paclitaxel, SB-T-1214,
SB-T-1214-fluorescein, BLT-S and ABTD conjugates

|  | ID-8 | MX-1 | WI-38 |
|---|---|---|---|
| Paclitaxel | 21.2 ± 4.30 | 3.83 ± 0.59 | 175 ± 51.6 |
| SB-T-1214 | 1.89 ± 0.30 | 2.90 ± 0.47 | 4.14 ± 0.82 |
| SB-T-1214-fluorescein (28) | 846 ± 112 | N.D. | 519 ± 156 |
| BLT-S (40) | 7.84 ± 1.85 | 26.7 ± 3.44 | 519 ± 90.3 |
| BLT-S (40) + GSH-OEt* | 5.91 ± 0.32 | 1.52 ± 0.34 | N.D. |
| ABTD-1 | 0.66 ± 0.03 | 2.05 ± 0.91 | 582 ± 48.8 |
| ABTD-1 + GSH-OEt* | 0.62 ± 0.07 | 0.12 ± 0.05 | N.D. |
| ABTD-2 | >5000 | 3630 ± 1300 | N.D. |
| ABTD-2 + GSH-OEt* | 651 ± 169 | 411 ± 80.9 | N.D. |
| ABTD-3 | >5,000 | >5,000 | N.D. |

The concentration of cytotoxic compounds that inhibit 50% ($IC_{50}$, nM) of different types of cells after 72 hours of drug exposure at 37° C. under 5% $CO_2$ was examined.
(BLT-S is biotin-$PEG_3$-linker-taxoid).
*24 h of drug exposure, followed by thorough washing with DPBS, and 48 hours incubation with 6 equivalents of glutathione-OEt at 37° C. under 5% $CO_2$.
N.D. = not determined.

The cytotoxicity assays of ABTD conjugates using the MTT method against ID-8, MX-1, and WI-38 cell lines were compared to that of paclitaxel and free taxoid SB-T-1214 and its fluorescein conjugate (28) as well as BLT-S (Biotin-$PEG_3$-linker-SB-T-1214). The results are summarized in Table 1.

As Table 1 shows, the $IC_{50}$ values of SB-T-1214 against ID-8, MX-1 and WI-38 are 1.89 nM, 2.90 nM and 4.14 nM, respectively, which is 1 to 2 orders of magnitude more potent than paclitaxel ($IC_{50}$ 21.2 nM, 3.83 nM, 175 nM, respectively). SB-T-1214 exhibited very similar $IC_{50}$ values against these three cell lines. Paclitaxel exhibited small differences in $IC_{50}$ values against the three cell lines. Thus, paclitaxel has appreciable selectivity difference between cancer cells and normal cells, but SB-T-1214 does not distinguish targeted cancer cells from normal cells.

Table 1 also shows that SB-T-1214-fluorescein conjugate (28) with modification at the C7 position exhibits 2 to 3 orders of magnitude less potency than SB-T-1214. Similar results were also observed from the comparison between ABTD-1 and ABTD-2 against ID-8 ($IC_{50}$ 0.66 nM, >5,000 nM, respectively) and MX-1 ($IC_{50}$ 2.05 nM, 3,630 nM, respectively).

ABTD-1 exhibited extraordinary and unexpected potency ($IC_{50}$ 0.66 nM), approximately three times more potent as compared to SB-T-1214 ($IC_{50}$ 1.89 nM) against ID-8, overexpressing biotin receptors, indicating the high efficiency of this ABTD platform to deliver cytotoxic agents, which is consistent with the results from CFM and flow cytometry (FIGS. 4 and 5). With the addition of 6 equivalents of glutathione-ethyl ester to fully cleave the linker and release all the cytotoxic agents, the $IC_{50}$ did not change significantly ($IC_{50}$ 0.62 nM), indicating endogenous glutathione level (and possibly some other thiols) was sufficient to cleave all the internalized ABTD conjugate in 72 h incubation. ABTD-1 shows similar potency as SB-T-1214 against MX-1 ($IC_{50}$ 2.05 nM, 2.90 nM, respectively) without the addition of glutathione-ethyl ester. However, ABTD-1 exhibited one order of magnitude higher potency ($IC_{50}$ 0.12 nM) once 6 equivalents of glutathione-ethyl ester were added and incubated for another 48 hours, indicating the insufficient endogenous glutathione level in MX-1 cells.

ABTD-1 and BLT-S exhibited a similar weak potency against the WI-38 cell line (biotin receptor is not overexpressed), showing that excellent tumor-targeting efficiency using the biotin receptor as tumor-specific target via RME was clearly achieved by these conjugates. However, ABTD-1 exhibited more than two orders of magnitude weaker cytotoxicity against WI-38 ($IC_{50}$ 582 nM), which demonstrates that ABTD-1 has even higher (more than 10 times) cancer cell selectivity that that of BLT-S.

ABTD-1 exhibits approximately ten times higher potency than BLT-S (single TTM with single cytotoxic/warhead agent conjugate) against ID-8 cell line ($IC_{50}$ 0.66 nM and 2.05 nM, respectively), and MX-1 cell line ($IC_{50}$ 7.84 nM and 26.7 nM, respectively). Similar results were also observed with the addition of 6 equivalents of glutathione-ethyl ester. Therefore, higher intracellular concentration of warhead (cytotoxic agent) was achieved utilizing the dendrimer platform with multiple cytotoxic agent moieties, and resulted in the surprisingly higher potency of the dendrimer-based conjugate with a lower dosage.

To assess a possible cytotoxicity of dendrimer itself as macromolecular vehicle, a cytotoxicity assay, using ABTD-3 which only has TTM and fluorescein moiety without warhead, was performed. As Table 1 clearly demonstrates, the $IC_{50}$ values of ABTD-3 against ID-8 and MX-1 are both over 5,000 nM, indicating the cytotoxicity of dendrimer platform is non-toxic and biocompatible.

The invention claimed is:

1. A dendrimer-based conjugate of the formula $V_m$-D-C-D'-(T-F)$_n$, wherein:

V is a tumor-targeting molecule selected from the group consisting of biotin, antibodies, fragments of antibodies, monoclonal antibodies, a protein, a peptide, oligopeptides, aptamers, hyaluronic acid, lectin, a saccharide, a hormone, polyunsaturated fatty acids, folic acid, and transferrin or a neurotransmitter optionally substituted with polyethylene glycol, wherein a polyethylene glycol linker is situated between V and D;

m and n are the same or different are 1 to 64;

D is a half-dendron selected from the group consisting of PAMAM (poly(amidoamine)), PAMAMOS (poly(amidoamine-organosilicon)dendrimers), PPI (poly(propylene imine)), amphiphilic dendrimer, chiral dendrimer, multilingual dendrimer, micellar dendrimer, Tecto dendrimer and Frechet type dendrimer;

C is a PEGylated bis-maleimido spacer;

D' is as defined in D;

T is a cytotoxic agent selected from the group consisting of paclitaxel, taxoids, antimetabolites, anthracyclines, camptothecins, and vinca alkaloids; and F is a fluorescent tagging molecule selected from the group consisting of fluorescein and its derivatvies, rhodamine and its derivatives, coumarin and its derivatives, boron dipyrromethane fluorophore derivatives, naphthalimide derivatives, maleimide and its derivatives, and radionuclides.

2. The conjugate of claim 1, wherein V is biotin.

3. The conjugate of claim 1, wherein D and D' are half-dendrons of PAMAM.

4. The conjugate of claim 3, wherein D is a half-dendron G3 PAMAM and D' is a half-dendron of G1 PAMAM.

5. The conjugate of claim 1, wherein T is selected from taxoids.

6. The conjugate of claim 5, wherein said taxoid is SB-T-1214.

7. The conjugate of claim 1, wherein F is fluorescein.

8. The conjugate of claim 1, wherein m is 16 and n is 4.

9. The conjugate of claim 1, wherein the conjugate is ABTD-1.

10. The conjugate of claim 1, wherein the conjugate is ABTD-2.

11. A method of treating gastrointestinal cancers, breast cancer or lung cancer comprising administering to a patient in need thereof a dendrimer-based conjugate of the formula Vm-D-C-D'-(T-F)n, wherein:

V is a tumor-targeting molecule selected from the group consisting of biotin, antibodies, fragments of antibodies, fragments of antibodies, monoclonal antibodies, a protein, a peptide, oligopeptides, aptamers, hyaluronic acid, lectin, a saccharide, a hormone, polyunsaturated fatty acids, folic acid, and transferrin or a neurotransmitter optionally substituted with polyethylene glycol, wherein a polyethylene glycol linker is situated between V and D;

m and n are the same or different are 1 to 64;

D is a dendrimer selected from the group consisting of PAMAM (poly(amidoamine)), PAMAMOS (poly(amidoamine-organosilicon)dendrimers), PPI (poly(propylene imine)), amphiphilic dendrimer, chiral dendrimer, dendrimer, micellar dendrimer, Tecto dendrimer and Frechet type dendrimer;

C is a PEG fated bis-maleimido spacer;

D' is as defined in D;

T is a cytotoxic agent selected from the group consisting of taxoids, SB-T-1214, taxanes, paclitaxel, docetaxel, antimetabolites, anthracyclines, camptothecins, vinca alkaloids and platinums; and F is a fluorescent tagging molecule selected from the group consisting of fluorescein and its derivatvies, rhodamine and its derivatives, coumarin and its derivatives, boron dipyrromethane fluorophore derivatives, naphthalimide derivatives, maleimide and its derivatives, and radionuclides.

12. The method of claim 11, wherein V is biotin.

13. The method of claim 11, wherein D and D' are a half-dendron of PAMAM.

14. The method of claim 13, wherein D is a half-dendron of G3 PAMAM and D' is a half-dendron of G1 PAMAM.

15. The method of claim 11, wherein T is selected from taxoids.

16. The method of claim 15, wherein said taxoid is SB-T-1214.

17. The method of claim 11, wherein F is fluorescein.

18. The method of claim 11, wherein in is 16 and n is 4.

19. The method of claim 11, wherein the conjugate is selected from the group of ABTD-1 and ABTD-2.

20. A dendrimer-based conjugate of the formula $V_m$-D-C-D'$(T)_n$, wherein:

V is a tumor-targeting molecule selected from the group consisting of biotin, antibodies, fragments of antibodies, monoclonal antibodies, a protein, a peptide, oligopeptides, aptamers, hyaluronic acid, lectin, a saccharide, a hormone, polyunsaturated fatty acids, folic acid, and transferrin or a neurotransmitter optionally substituted with polyethylene glycol, wherein a polyethylene glycol linker is situated between V and D;

m and n are the same or different are 1 to 64;

D is a half-dendron selected from the group consisting of PAMAM (poly(amidoamine)), PAMAMOS (poly(amidoamine-organosilicon)dendrimers), PPI (poly(propylene imine)), amphiphilic dendrimer, chiral dendrimer, multilingual dendrimer, micellar dendrimer, Tecto dendrimer and Frechet type dendrimer;

C is a PEGylated bis-maleimido spacer;

D' is as defined in D; and

T is a cytotoxic agent selected from the group consisting of paclitaxel, toxoids, antimetabolites, anthracyclines, camptothecins, and vinca alkaloids.

21. A method of treating gastrointestinal cancers, breast cancer or lung cancer comprising administering to a patient in need thereof a dendrimer-based conjugate of the formula $V_m$-D-C-D'-$(T)_n$, wherein:

V is a tumor-targeting molecule selected from the group consisting of biotin, antibodies, fragments of antibodies, monoclonal antibodies, a protein, a peptide, oligopeptides, aptamers, hyaluronic acid, lectin, a saccharide, a hormone, polyunsaturated fatty acids, folic acid, and transferrin or a neurotransmitter optionally substituted with polyethylene glycol, wherein a polyethylene glycol linker is situated between V and D;

m and n are the same or different are 1 to 64,

D is a half-dendron selected from the group consisting of PAMAM (poly(amidoamine)), PAMAMOS (poly(amidoamine-organosilicon)dendrimers), PPI (poly(propylene imine)), amphiphilic dendrimer, chiral dendrimer, multilingual dendrimer, micellar dendrimer, Tecto dendrimer and Frechet type dendrimer;

C is a PEGylated bis-maleimido spacer;

D' is as defined in D; and

T is a cytotoxic agent selected from the group consisting of paclitaxel, taxoids, antimetabolites, anthracyclines, camptothecins, and vinca alkaloids.

\* \* \* \* \*